(12) United States Patent
Luo et al.

(10) Patent No.: US 8,298,765 B2
(45) Date of Patent: Oct. 30, 2012

(54) MULTIFUNCTIONAL NUCLEIC ACID NANO-STRUCTURES

(75) Inventors: Dan Luo, Ithaca, NY (US); Jong Bum Lee, Ithaca, NY (US)

(73) Assignee: Cornell University, Ithaca, NY (US)

( * ) Notice: Subject to any disclaimer, the term of this patent is extended or adjusted under 35 U.S.C. 154(b) by 247 days.

(21) Appl. No.: 12/651,275

(22) Filed: Dec. 31, 2009

(65) Prior Publication Data

US 2010/0183634 A1 Jul. 22, 2010

Related U.S. Application Data

(60) Provisional application No. 61/142,207, filed on Jan. 1, 2009.

(51) Int. Cl.
*C12Q 1/68* (2006.01)
*C12P 19/34* (2006.01)

(52) U.S. Cl. ........................................ 435/6.1; 435/91.1

(58) Field of Classification Search .................. None
See application file for complete search history.

(56) References Cited

U.S. PATENT DOCUMENTS

| | | | |
|---|---|---|---|
| 4,543,328 A | 9/1985 | Keller et al. | |
| 4,716,106 A | 12/1987 | Chiswell | |
| 5,288,609 A | 2/1994 | Engelhardt et al. | |
| 5,359,100 A | 10/1994 | Urdea et al. | |
| 5,386,020 A | 1/1995 | Seeman et al. | |
| 6,221,581 B1 | 4/2001 | Engelhardt et al. | |
| 6,261,779 B1 | 7/2001 | Barbera-Guillem et al. | |
| 6,265,021 B1 | 7/2001 | Black et al. | |
| 6,361,944 B1 | 3/2002 | Mirkin et al. | |
| 6,495,324 B1 | 12/2002 | Mirkin et al. | |
| 6,534,266 B1 | 3/2003 | Singer | |
| 6,689,374 B2 | 2/2004 | Chu et al. | |
| 6,974,669 B2 | 12/2005 | Mirkin et al. | |
| 7,052,650 B2 | 5/2006 | Strick et al. | |
| 7,223,544 B2 | 5/2007 | Luo et al. | |
| 7,405,044 B2 | 7/2008 | Walker et al. | |
| 2003/0036065 A1 | 2/2003 | Gellibolian | |
| 2004/0197845 A1 | 10/2004 | Hassibi et al. | |
| 2005/0019369 A1 | 1/2005 | Lyles | |
| 2005/0112578 A1 | 5/2005 | Matsuura et al. | |
| 2005/0130180 A1 | 6/2005 | Luo et al. | |
| 2006/0084607 A1 | 4/2006 | Spirio et al. | |
| 2007/0048759 A1 | 3/2007 | Luo et al. | |
| 2007/0117177 A1 | 5/2007 | Luo et al. | |
| 2007/0148246 A1 | 6/2007 | Luo et al. | |
| 2008/0167454 A1 | 7/2008 | Luo et al. | |
| 2009/0170124 A1 | 7/2009 | Campbell | |

OTHER PUBLICATIONS

International written opinion dated Oct. 19, 2010 for PCT Application No. US2009/69947.
International search report dated Oct. 19, 2010 for PCT Application No. US2009/69947.
Erben, et al. Single-molecule protein encapsulation in a rigid DNA cage. Angew Chem Int Ed Engl. Nov. 13, 2006;45(44):7414-7.
Goodman, et al. Reconfigurable, braced, three-dimensional DNA nanostructures. Nat Nanotechnol. Feb. 2008;3(2):93-6.
Goodman, R. NANEV: A program employing evolutionary methods for the design of nucleic acid nanostructures. Biotechniques. Apr. 2005;38(4):548, 550.
Labean, et al. Constructing novel materials with DNA. Nanotoday. Apr. 2007; 2(2):26-35.
Rothemund, et al. Folding DNA to create nanoscale shapes and patterns. Nature. Mar. 16, 2006;440(7082):297-302.

*Primary Examiner* — James Martinell
(74) *Attorney, Agent, or Firm* — Wilson Sonsini Goodrich & Rosati

(57) ABSTRACT

Compositions and methods are provided for constructing multi-functional nucleic acid nano-structures. Nano-structures are provided incorporating a built-in modularity, including nucleic acid modules. Modules contain moieties including detectible labels, nanoparticles, reactive moieties and other functional groups. Nano-structures can be used for delivery of target compounds, as well as identification of target nucleic acid molecules.

18 Claims, 24 Drawing Sheets

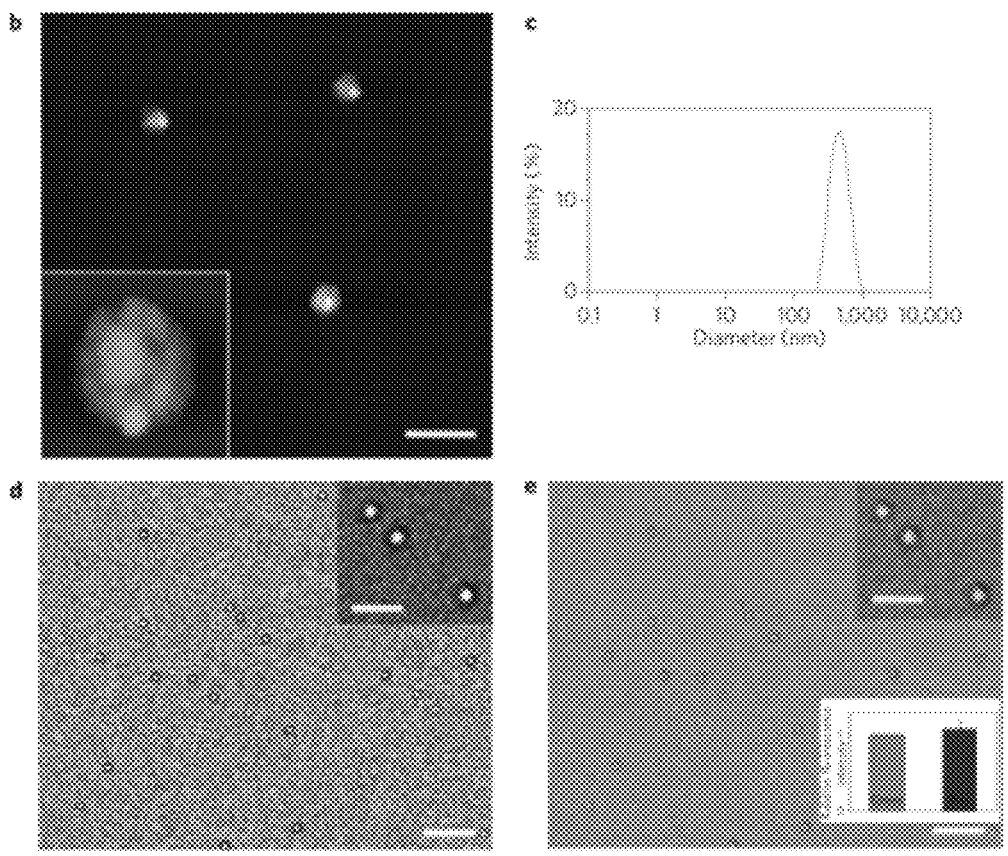
FIG. 2B-E

FIG. 4A-B

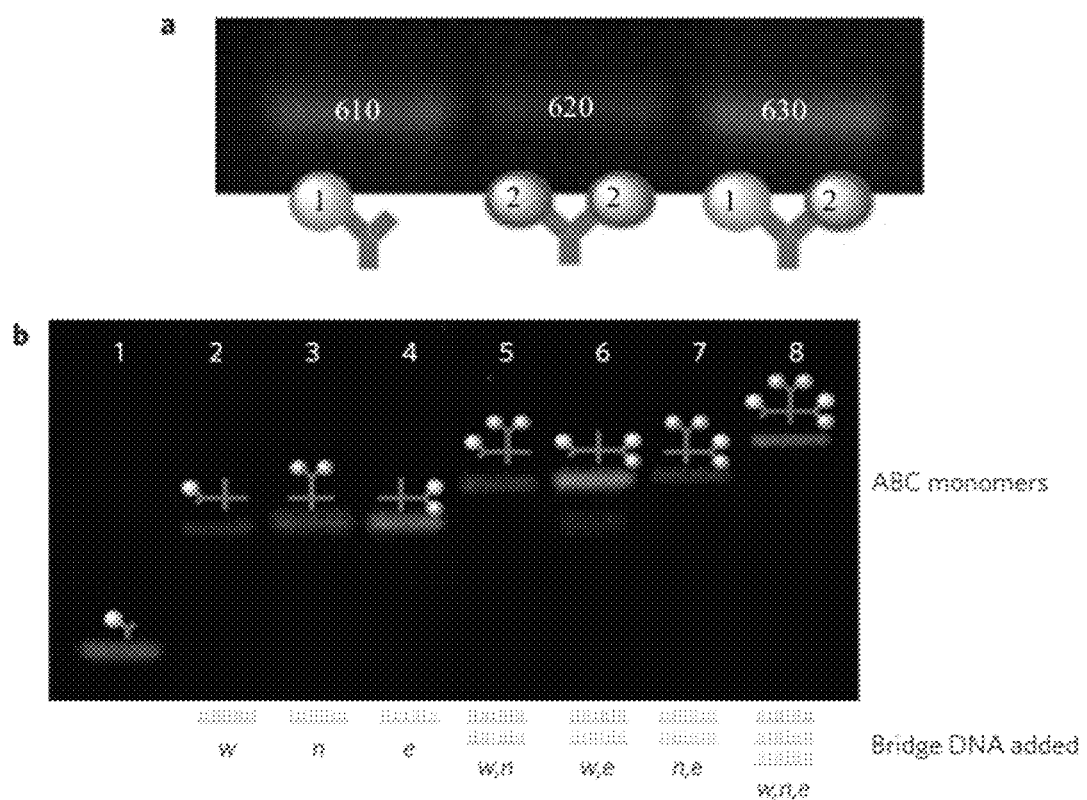
FIG. 6A-B

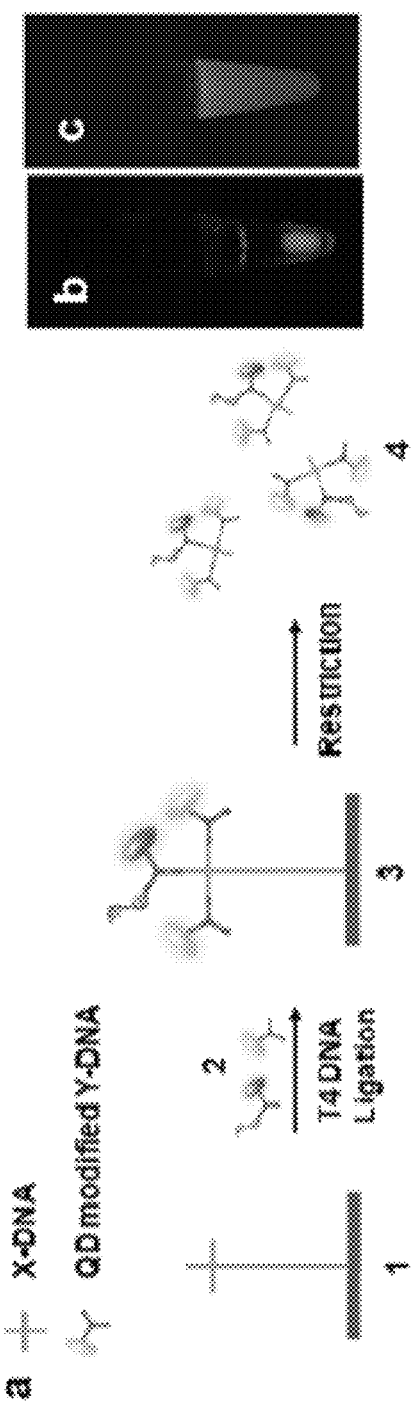
FIG. 9A-C

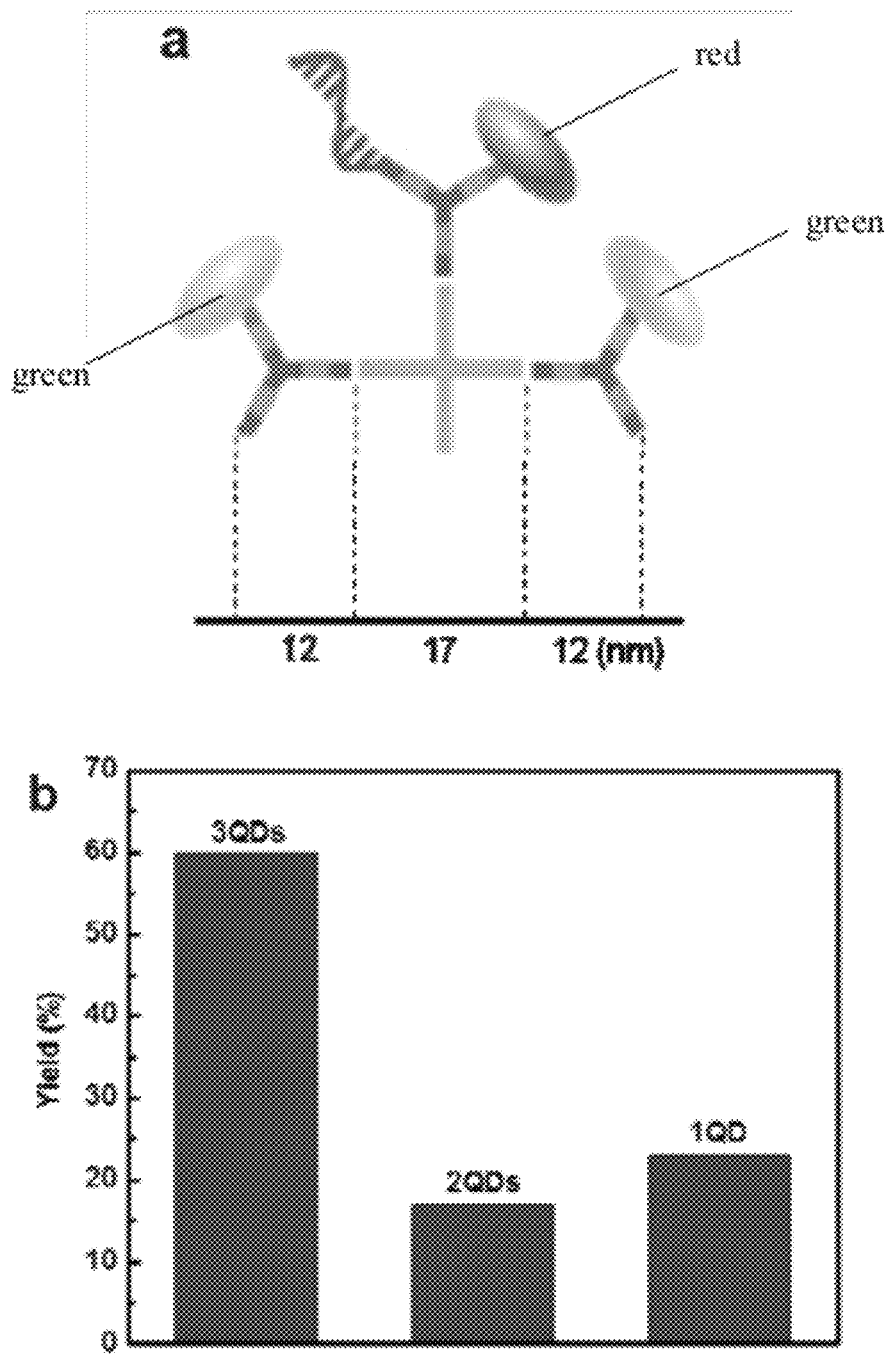
FIG. 10A-B

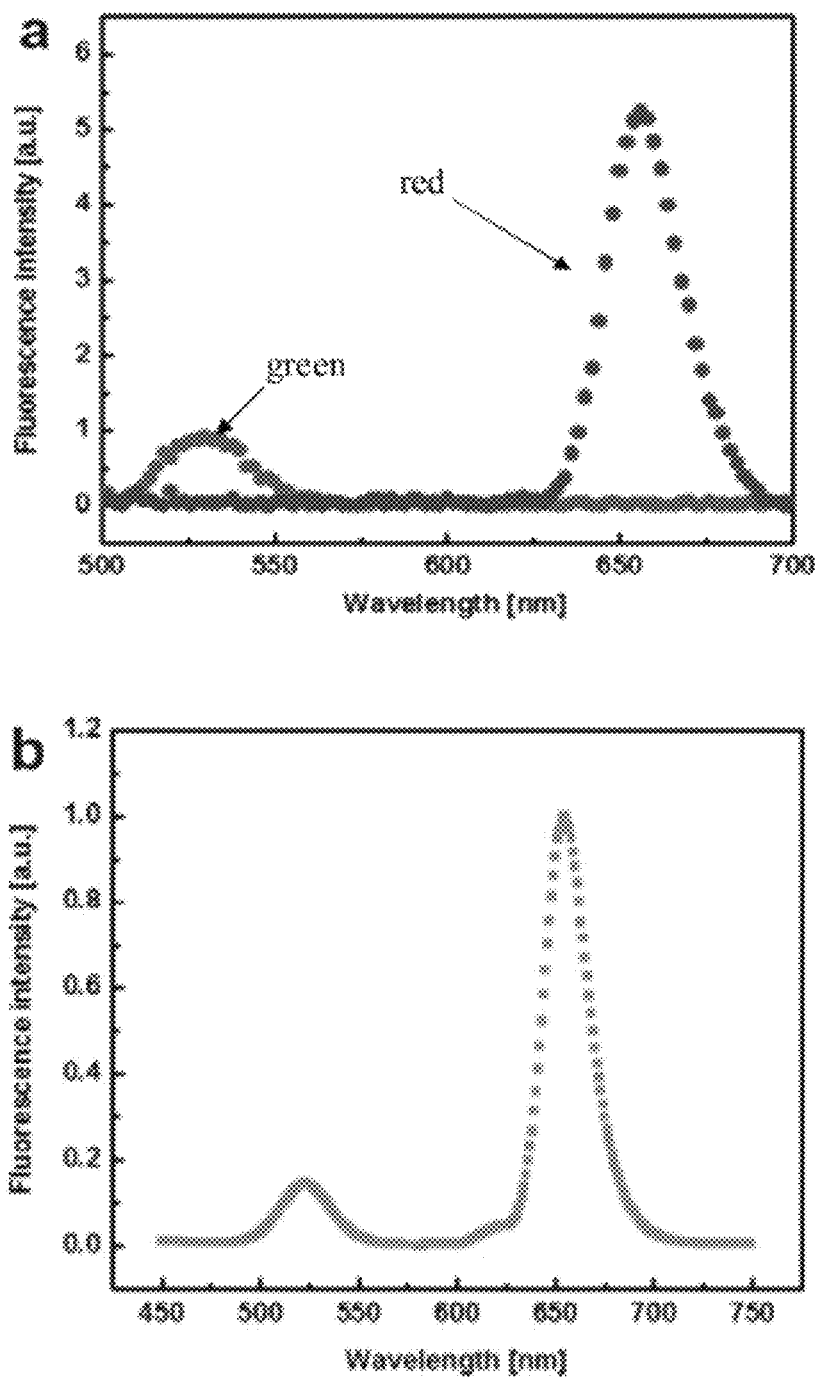
FIG. 11A-B

| Strand | | Sequence | |
|---|---|---|---|
| Target (Ban) DNA | | 5'-GGATTATTGTTAAATATTGATAAGGAT-3' | |
| Target (Ebo) DNA | | 5'-CATGTCAGTGATTATTATAACCCACCA-3' | |
| Target (Sars) DNA | | 5'-ATAATACTGCGTCTTGGTTCACAGC-3' | |
| Unrelated DNA | | 5'-AGATGCAATAGTAATCAGGTAGAGACG-3' | |
| Y-DNA (Probe1) | Y₀₁(Ban) | 5'-TTAACAATAATCC | GCCACTGGATCCGCATGAGGTAGGACGACATTCG CCGTAAGCACAC-3' |
| | Y₀₁(Ebo) | 5'-AATCACTGACATG | |
| | Y₀₁(Sars) | 5'-GACGCAGTATTAT | |
| | Y₀₂ (Biotin) | 5'-Biotin-C₆-GTGTGCTTACGGCGAATGTCGTCACAGCACCGAATCAGCCTGT CGA-3' | |
| | Y₀₃ | 5'-/Phos/-GGATTCGACAGGCTGATTCGGTGCTGTCTACCTCATGCGGATCCAGT GGC-3' | |
| Y-DNA (probe2) | Y₀₁ | 5'-GCCACTGGATCCGCATGAGGTAGGACGACATTCGCCGTAAGCACAC-3' | |
| | Y₀₂ (Biotin) | 5'-Biotin-C₆-GTGTGCTTACGGCGAATGTCGTCACAGCACCGAATCAGCCTG TCGA-3' | |
| | Y₀₃(Ban) | 5'-/Phos/-GGATTCGACAGGCTGATTCGGTGCTGTCT ACCTCATGCGGATCCAGTGGC | ATCCTTATCAATAT-3' |
| | Y₀₃(Ebo) | | TGGTGGGTTATAAT-3' |
| | Y₀₃(Sars) | | GCTGTGAACCAA-3' |
| Y-DNA (NH₂) | Y₀₁ | 5'-GCCACTGGATCCGCATGAGGTAGGACGACATTCGCCGTAAGCACAC-3' | |
| | Y₀₂ | 5'-/NH₂/GTGTGCTTACGGCGAATGTCGTCACAGCACCGAATCAGCCTGTCGA-3' | |
| | Y₀₃ | 5'-/Phos/-TTGCTCGACAGGCTGATTCGGTGCTGTCTACCTCATGCGGATCCAGT GGC-3' | |

Note that /phos/ represents the phosphorylation on the 5' end of the oligonucleotide.

FIG. 12

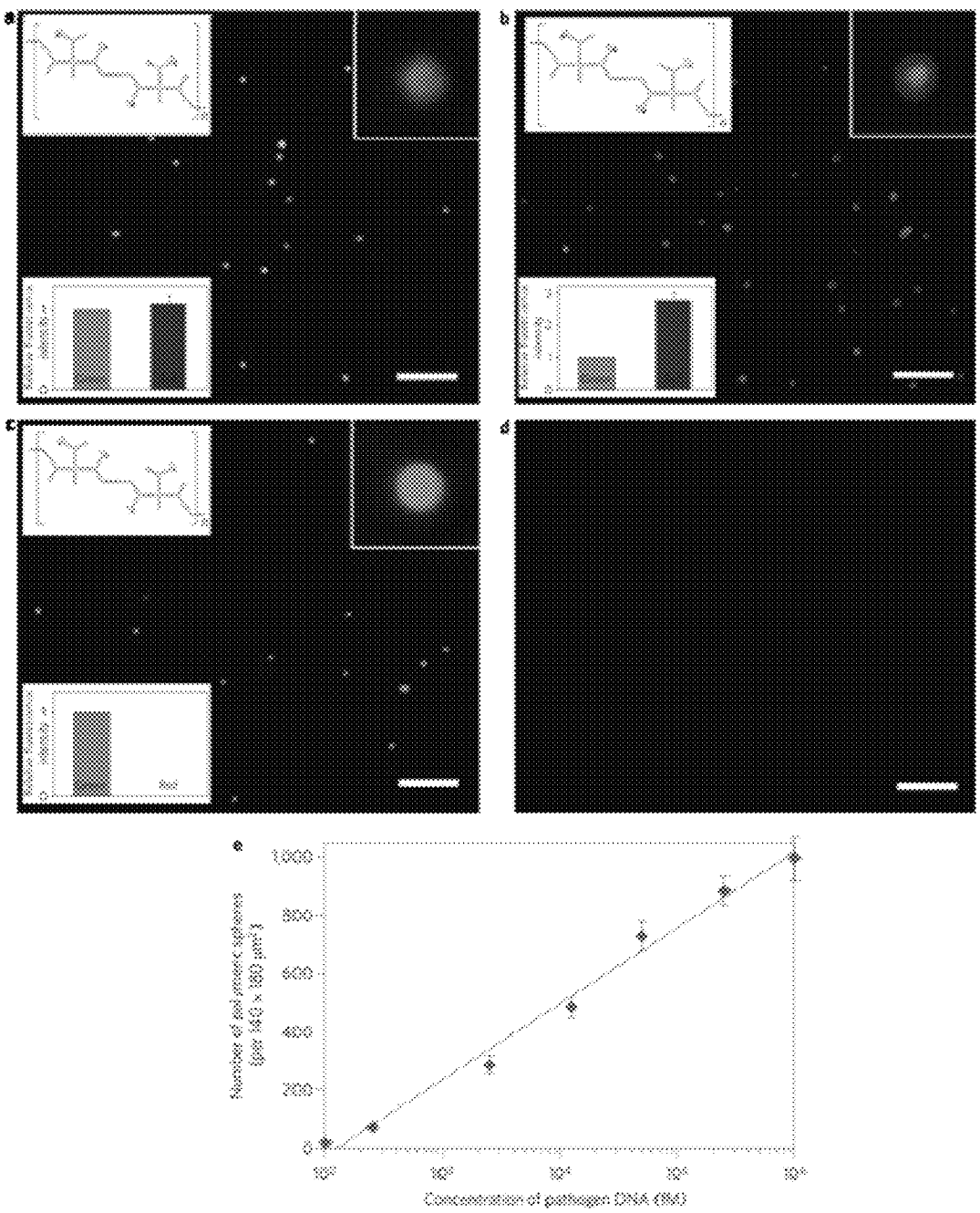
FIG. 13A-E

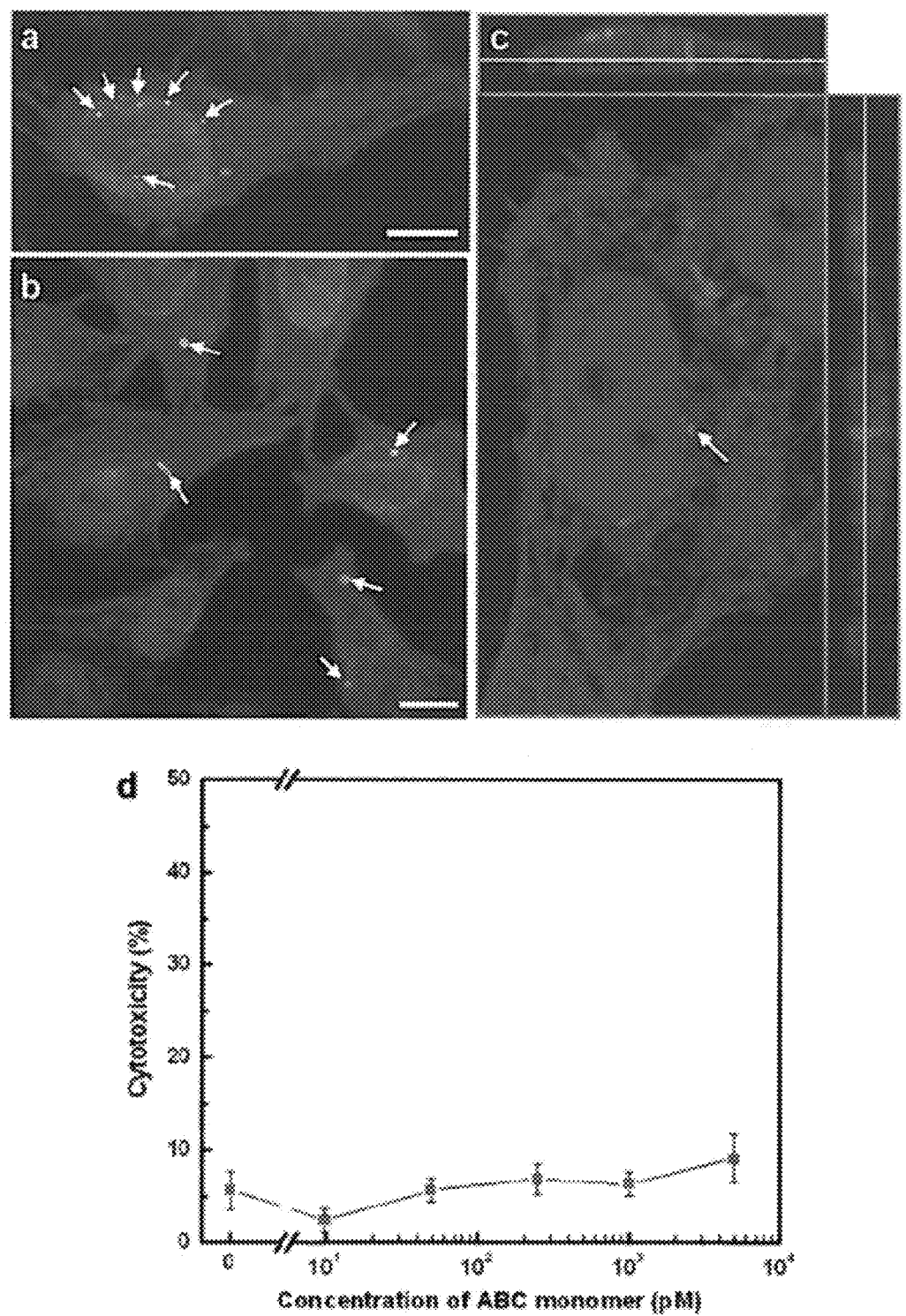
FIG. 14A-D

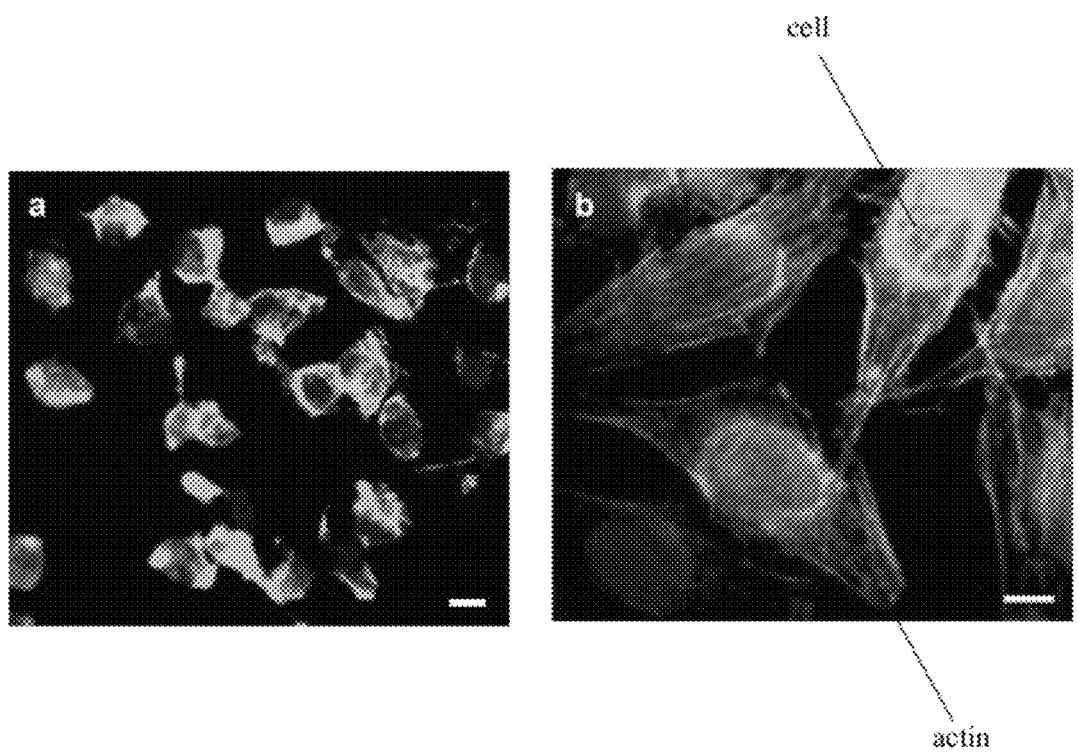
FIG. 15A-B

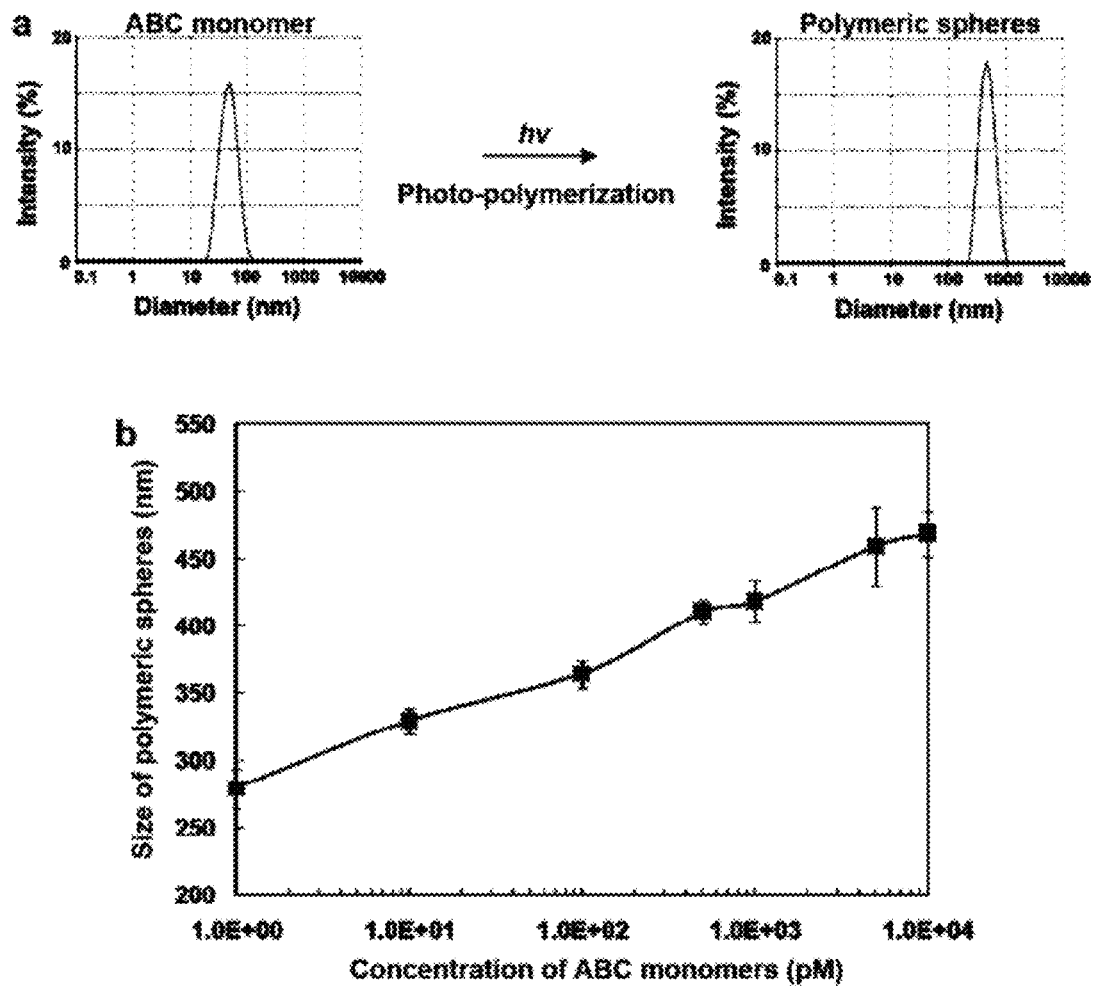
FIG. 18A-B

| Strand | | Sequence |
|---|---|---|
| X DNA | $X_{01}$ | 5'-CGACCGATGAATAGCGGTCAGATCCGTACCTACTCGCTCA-3' |
| | $X_{02}(W')$ | 5'-CGAGACCATACGTACAGCACCCGTATTCATCGGTCGTGGTGGGTTATAAT-3' |
| | $X_{03}(N')$ | 5'-CGAGTCCGTTCGCAATACGGCTGTACGTATGGTCTCGCGTCTCTACCTGAT-3' |
| | $X_{04}(E')$ | 5'-/Phos/-CGAGTAGGTACGGATCTGCGTATTGCGAACGACTCGGCTGTGAACCAAG-3' |
| Bridge DNA (w) | | 5'-CATGTCAGTGATTATTATAACCCACCA-3' |
| Bridge DNA (n) | | 5'-AGATGCAATAGTAATCAGGTAGAGACG-3' |
| Bridge DNA (e) | | 5'-ATAATACTGCGTCTTGGTTCACAGC-3' |
| Y DNA (W) | $Y_{01}(W)$ | 5'-AATCACTGACATGTGGATCCGCATGACATTCGCCGTAAG-3' |
| | $Y_{02}(●)$ | 5'-Alexa Fluor 488●-CTTACGGCGAATGACCGAATCAGCCT-3' |
| | $Y_{03}$ | 5'-AGGCTGATTCGGTTCATGCGGATCCA-3' |
| Y DNA (N) | $Y_{01}(N)$ | 5'-TACTATTGCATCTXXXATCCGCATGACATTCGCCGTAAG-3' |
| | $Y_{04}(●)$ | 5'-BODIPY630/650●-CTTACGGCGAATGACCGAATCAGCCT-3' |
| | $Y_{05}(●)$ | 5'-BODIPY630/650●-AGGCTGATTCGGTTCATGCGGATCCA-3' |
| Y DNA (E) | $Y_{01}(E)$ | 5'-ACGCAGTATTATTGGATCCGCATGACATTCGCCGTAAG-3' |
| | $Y_{02}(●)$ | 5'-Alexa Fluor 488●-CTTACGGCGAATGACCGAATCAGCCT-3' |
| | $Y_{05}(●)$ | 5'-BODIPY630/650●-AGGCTGATTCGGTTCATGCGGATCCA-3' |
| SP DNA | $SP_{01}$ | 5'-Biotin-C₆-CCGGATAAGGCGCAGCCGGTCGGCTGAATTCAGGGTTCGTGGCAGGCCAGCACACTTGGAGACCGAAGCTTACCGGACTCCTAACTGAG-3' |
| | $SP_{02}$ | 5'-/Phos/-GTTAGGAGTCCGGTAAGCTTCGGTCTCCAAGTGTGCTGGCCTGCCACGAACCCTGAATTCAGCCGACCGGCTGCGCCTTATCCGG-3' |

FIG. 19

| Strand | | Sequence |
|---|---|---|
| X DNA | X01 | 5'-/Phos/-TGAGCACCGATGAATAGCGGTCAGATCCGTACCTACTCG-3' |
| | X02 | 5'-/Phos/-ATCCCGAGTAGGTACCGATCTGCGTATTGCGAACGACTCG-3' |
| | X03 | 5'-/Phos/-GCAACGAGTCGTTCGCAATACGGCTGTACGTATGGTCTCG-3' |
| | X04 | 5'-/Phos/-GAGTCGAGACCATACGTACAGCACCGCTATTCATCGGTGC-3' |
| Template DNA | | 5'-TTACGGAGGTGGTTGTGGCA-A$_{10}$-C$_3$-SH-3' |
| Y DNA (QD) | Y01 | 5'-GCCACTGGATCCGCATGAGGTAGGACGACATTCGCCGTAAGCACAC-3' |
| | Y02 (Biotin) | 5'-Biotin-C$_6$-GTGTGCTTACGGCGAATGTCGTCACAGCACCGAATCAGCCTGTCGA-3' |
| | Y03 | 5'-/Phos/-GGAT TCGACAGGCTGATTCGGTGCTGTCTACCTCATGCGGATCCAGT<br>5'-/Phos/-ACTC GGC-3' |
| Y DNA (AuNP) | Y31 | 5'-GCCACAACCACCTCCGTAAGCCACTGGATCCGCATGAGGTAGGACGACAT TCGCCGTAAGCACAC-3' |
| | Y32 | 5'-GTGTGCTTACGGCGAATGTCGTCACAGCACCGAATCAGCCTGTCGA-3' |
| | Y33 | 5'-/Phos/-TTGCTCGACAGGCTGATTCGGTGCTGTCTACCTCATGCGGATCCAGTGGC-3' |
| SP DNA | SP01 | 5'-Biotin-C$_6$-CCGGATAAGGCGCAGCGGTCGGCTGAATTCAGGGTTCGTGCCAG GCCAGCACACTTGGAGACCGAAGCTTACCGGACTCCTAAC-3' |
| | SP02 | 5'-/Phos/-TCAGTTAGGAGTCCGGTAAGCTTCGGTCTCCAAGTGTGCTGGCCTGC CAC GAACCCTGAATTCAGCCGACCGCTGCGCCTTATCCGG-3' |

FIG. 20

| Polymeric sphere | ABC monomer 1 | ABC monomer 2 | Target DNA |
|---|---|---|---|
| 1G3R | 2R | 1G1R | Bacillus anthracis |
| 4G0R | 2G | 2G | Ebola virus |
| 2G2R | 1G1R | 1G1R | SARS Coronavirus |
| (No polymer formation) | 1G1R | 1G1R | Unrelated DNA |

FIG. 21

SEQUENCE LISTING

<160> NUMBER OF SEQ ID NOS: 49

<210> SEQ ID NO 1
<211> LENGTH: 27
<212> TYPE: DNA
<213> ORGANISM: Bacillus anthracis

<400> SEQUENCE: 1
ggattattgt taaatattga taaggat                                      27

<210> SEQ ID NO 2

-continued

<211> LENGTH: 27
<212> TYPE: DNA
<213> ORGANISM: Ebola virus

<400> SEQUENCE: 2
catgtcagtg attattataa cccacca                                    27

<210> SEQ ID NO 3
<211> LENGTH: 25
<212> TYPE: DNA
<213> ORGANISM: SARS coronavirus

<400> SEQUENCE: 3
ataatactgc gtcttggttc acagc                                      25

<210> SEQ ID NO 4
<211> LENGTH: 27
<212> TYPE: DNA
<213> ORGANISM: Unknown
<220> FEATURE:
<223> OTHER INFORMATION: Description of Unknown: Unrelated DNA sequence

<400> SEQUENCE: 4
agatgcaata gtaatcaggt agagacg                                    27

<210> SEQ ID NO 5
<211> LENGTH: 59
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ttaacaataa tccgccactg gatccgcatg aggtaggacg acattcgccg taagcacac     59

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
aatcactgac atggccactg gatccgcatg aggtaggacg acattcgccg taagcacac     59

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
gacgcagtat tatgccactg gatccgcatg aggtaggacg acattcgccg taagcacac     59

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8

```
gtgtgcttac ggcgaatgtc gtcacagcac cgaatcagcc tgtcga                        46
```

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9

```
ggattcgaca ggctgattcg gtgctgtcta cctcatgcgg atccagtggc                    50
```

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10

```
gccactggat ccgcatgagg taggacgaca ttcgccgtaa gcacac                        46
```

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11

```
gtgtgcttac ggcgaatgtc gtcacagcac cgaatcagcc tgtcga                        46
```

<210> SEQ ID NO 12
<211> LENGTH: 64
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12

```
ggattcgaca ggctgattcg gtgctgtcta cctcatgcgg atccagtggc atccttatca        60
atat                                                                      64
```

<210> SEQ ID NO 13
<211> LENGTH: 64
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13

```
ggattcgaca ggctgattcg gtgctgtcta cctcatgcgg atccagtggc tggtgggtta        60
taat                                                                      64
```

<210> SEQ ID NO 14
<211> LENGTH: 62
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 14
ggattcgaca ggctgattcg gtgctgtcta cctcatgcgg atccagtggc gctgtgaacc      60
aa                                                                     62

<210> SEQ ID NO 15
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gccactggat ccgcatgagg taggacgaca ttcgccgtaa gcacac                     46

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtgtgcttac ggcgaatgtc gtcacagcac cgaatcagcc tgtcga                     46

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ttgctcgaca ggctgattcg gtgctgtcta cctcatgcgg atccagtggc                 50

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgaccgatga atagcggtca gatccgtacc tactcgctca                            40

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgagaccata cgtacagcac cgctattcat cggtcgtggt gggttataat                 50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 20
cgagtcgttc gcaatacggc tgtacgtatg gtctcgcgtc tctacctgat          50

<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cgagtaggta cggatctgcg tattgcgaac gactcggctg tgaaccaag           49

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
catgtcagtg attattataa cccacca                                   27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agatgcaata gtaatcaggt agagacg                                   27

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ataatactgc gtcttggttc acagc                                     25

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aatcactgac atgtggatcc gcatgacatt cgccgtaag                      39

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
```

```
cttacggcga atgaccgaat cagcct                                              26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aggctgattc ggttcatgcg gatcca                                              26

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tactattgca tcttggatcc gcatgacatt cgccgtaag                                39

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cttacggcga atgaccgaat cagcct                                              26

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aggctgattc ggttcatgcg gatcca                                              26

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
acgcagtatt attggatccg catgacattc gccgtaag                                 38

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cttacggcga atgaccgaat cagcct                                              26
```

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
aggctgattc ggttcatgcg gatcca                                          26

<210> SEQ ID NO 34
<211> LENGTH: 88
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
ccggataagg cgcagcggtc ggctgaattc agggttcgtg gcaggccagc acacttggag      60
accgaagctt accggactcc taactgag                                        88

<210> SEQ ID NO 35
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
gttaggagtc cggtaagctt cggtctccaa gtgtgctggc ctgccacgaa ccctgaattc      60
agccgaccgc tgcgccttat ccgg                                            84

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
tgagcaccga tgaatagcgg tcagatccgt acctactcg                            39

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
atcccgagta ggtacggatc tgcgtattgc gaacgactcg                           40

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38

```
gcaacgagtc gttcgcaata cggctgtacg tatggtctcg                              40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gagtcgagac catacgtaca gcaccgctat tcatcggtgc                              40

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttacggaggt ggttgtggca aaaaaaaaa                                          30

<210> SEQ ID NO 41
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gccactggat ccgcatgagg taggacgaca ttcgccgtaa gcacac                       46

<210> SEQ ID NO 42
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gtgtgcttac ggcgaatgtc gtcacagcac cgaatcagcc tgtcga                       46

<210> SEQ ID NO 43
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggattcgaca ggctgattcg gtgctgtcta cctcatgcgg atccagtggc                   50

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
actctcgaca ggctgattcg gtgctgtcta cctcatgcgg atccagtggc                   50
```

```
<210> SEQ ID NO 45
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gccacaacca cctccgtaag ccactggatc cgcatgaggt aggacgacat tcgccgtaag      60
cacac                                                                  65

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtgtgcttac ggcgaatgtc gtcacagcac cgaatcagcc tgtcga                     46

<210> SEQ ID NO 47
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttgctcgaca ggctgattcg gtgctgtcta cctcatgcgg atccagtggc                 50

<210> SEQ ID NO 48
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccggataagg cgcagcggtc ggctgaattc agggttcgtg gcaggccagc acacttggag      60
accgaagctt accggactcc taac                                             84

<210> SEQ ID NO 49
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tcagttagga gtccggtaag cttcggtctc caagtgtgct ggcctgccac gaaccctgaa      60
ttcagccgac cgctgcgcct tatccgg                                          87
```

MULTIFUNCTIONAL NUCLEIC ACID NANO-STRUCTURES

The application claims the benefit of U.S. Provisional Patent Application No. 61/142,207 to Luo et al., filed on Jan. 1, 2009, which is entirely incorporated herein by reference.

SEQUENCE LISTING

The instant application contains a Sequence Listing which has been submitted via EFS-Web and is hereby incorporated by reference in its entirety. Said ASCII copy, created on Mar. 23, 2010, is named 32497717.txt and is 12,014 bytes in size.

BACKGROUND OF THE INVENTION

Molecules of biological systems, such as, for example, nucleic acids, have the potential of serving as building blocks for the construction of new biological materials (or biomaterials), including individual geometrical objects, nanomechanical devices, and extended constructions that permit the fabrication of intricate structures of materials to serve many practical purposes, such as, e.g., pathogen detection and delivery of biologically active agents. This is at least in part due to their self and programmable-assembly capabilities.

Deoxyribonucleic acid ("DNA") and ribonucleic acid ("RNA") nucleic acid molecules possess distinct mechanical, physical, and chemical properties. From a mechanical point of view, DNA molecules can be rigid (e.g., when the molecules are less than 50 nm, the persistent length of double stranded DNA), or flexible. Physically, DNA is small, with a width of about 2 nanometers and a length of about 0.34 nanometers per base pair (for B-DNA). DNA can have various shapes, such as linear and circular shapes. Chemically, DNA is generally stable, non-toxic, water soluble, and commercially available in large quantities and high purity. Moreover, DNA molecules can be easily and highly manipulated by various well-known enzymes, such as restriction enzymes and ligases.

Under proper conditions, DNA and RNA molecules can self-assemble with complementary strands of nucleic acid (e.g., DNA, RNA, or Peptide Nucleic Acid, (PNA)), proteins or peptides. DNA molecules can be amplified exponentially and ligated specifically. Thus, DNA (and RNA) is an excellent candidate for constructing nano-material.

The ability to attach different functional moieties to a molecular building block can lead to applications in various fields. Multiple functionalities can be obtained by assembling different moieties onto a core building block leading to applications in nanoelectronics, intelligent sensing, and drug delivery. The combined functionalities can be synergistic.

To attach different moieties onto a building block, the core block is typically multivalent, anisotropic, or both multivalent and anisotropic. Although many anisotropic building blocks have been created, there lacks a universal anisotropic building block. A core block that is both multivalent and anisotropic can increase the precision of attaching different moieties onto a building block.

DNA has been used to generate various nano-structures. In addition, DNA has been used as a general building block material. Still, there exists a need for building blocks that can be used to build nano-structures with increased precision to create structures that are multifunctional, and in some embodiments, synergistically multifunctional.

SUMMARY OF THE INVENTION

The invention relates to nucleic acid polymerization and biological nano-structures, including target-driven nucleic acid polymerization and biological nano-structures for nucleic acid detection, e.g., pathogenic DNA, and delivery of biologically active agents.

In an aspect, the invention provides a composition comprising an X-shaped nucleic acid hybridized to one or more Y-shaped nucleic acids, wherein the composition comprises a sequence that is complementary to a target nucleic acid. The target can be a nucleic acid indicative of a condition, e.g, the presence of a pathogenic organism, disease state or environmental contaminant. The composition can be designed to specifically hybridize to the target and to avoid hybridization to background nucleic acids. Background includes without limitation uninformative cellular DNAs or mRNAs, or nucleic acids of the composition.

In another aspect, the invention provides a composition comprising: a first monomer comprising a first X-shaped nucleic acid, a first Y-shaped nucleic acid and a second Y-shaped nucleic acid, wherein the first Y-shaped nucleic acid comprises a linker sequence that is complementary to a first portion of a sequence of a target nucleic acid and the second Y-shaped nucleic acid comprises a crosslinkable moiety; and a second monomer comprising the first X-shaped nucleic acid or a second X-shaped nucleic acid, a third Y-shaped nucleic acid and a fourth Y-shaped nucleic acid, wherein the third Y-shaped nucleic acid comprises a linker sequence that is complementary to a second portion of the sequence of the target nucleic acid and the fourth Y-shaped nucleic acid comprises a crosslinkable moiety.

In some embodiments, the first X-shaped nucleic acid is linked to the first and second Y-shaped nucleic acids. In some embodiments, the first X-shaped nucleic acid is linked to the first and/or second Y-shaped nucleic acid with the aid of bridge DNA having a sequence that is complementary to a donor sequence of the first and/or second Y-shaped nucleic acid, respectively, and an acceptor sequence of the first X-shaped nucleic acid. In some embodiments, the second X-shaped nucleic acid is linked to the third and fourth Y-shaped nucleic acids. In some embodiments, the second X-shaped nucleic acid is linked to the third and/or fourth Y-shaped nucleic acid with the aid of a bridge DNA having a sequence that is complementary to a donor sequence of the third and/or fourth Y-shaped nucleic acid, respectively, and the acceptor sequence of the second X-shaped nucleic acid. The first or second monomer may comprise a fifth Y-shaped nucleic acid.

In some embodiments, the crosslinkable moiety of the second Y-shaped nucleic acid and the crosslinkable moiety of the fourth Y-shaped nucleic acid are photo-crosslinkable moieties. In some embodiments, the crosslinkable moiety of the second Y-shaped nucleic acid is configured to crosslink with the crosslinkable moiety of the fourth Y-shaped nucleic acid.

In some embodiments, the first monomer is configured to link to the second monomer when in the presence of the target nucleic acid. For example, the first and second monomers can be configured to form a dimer, and the dimer can be further configured to form a polymer.

The nucleic acids of the invention, e.g., the X-shaped and Y-shaped nucleic acids, can comprise deoxyribonucleic acid (DNA), ribonucleic acid (RNA), peptide nucleic acid (PNA), or a combination thereof.

In some embodiments, one or more of the nucleic acids of the subject compositions, e.g., X-shaped or Y-shaped nucleic acid, comprise a functional moiety. The functional moiety can be without limitation a DNA capture probe, a fluorescent dye, a quantum dot, a gold nanoparticle, a peptide, a polypeptide, a protein, a lipid, a carbohydrate, an aptamer, an antibody, an antigen, a cell growth factor, a DNA binding agent, a detectable label, a selectable marker, biotin, a biologically active agent, a pharmaceutical agent, a drug, a small molecule, a therapeutic agent, a receptor molecule, a ligand, a nucleic acid molecule or a substrate.

The target nucleic acid recognized by the compositions of the invention, e.g., by complementary base pairing, may comprise without limitation a nucleic acid sequence from a host cell, a bacterium, a virus, a protozoan, a yeast, a fungus, or a parasite.

In another aspect, the invention provides a method for detecting a target nucleic acid, comprising: a) forming a mixture by contacting one or more nucleic acids with a composition of the invention; and b) subjecting the mixture to a stimulus capable of inducing a polymerization reaction between dimers formed between the composition and the target nucleic acid.

In some embodiments, the method further comprises detecting the presence of a polymer comprising the composition. The polymer can also comprise the target nucleic acid.

In some embodiments, detecting the presence of the polymer comprises detecting the presence of one or more functional moieties linked to the composition. For example, detecting the presence of the polymer may comprise detecting fluorescent light emanating from the mixture, e.g., from a fluorescent moiety linked to the composition.

In some embodiments, the stimulus capable of inducing a polymerization reaction comprises electromagnetic radiation. For example, the electromagnetic radiation may comprise ultraviolet (UV) light, visible light, near infrared, infrared, microwaves, gamma rays, X-rays, or radio waves.

In some embodiments, the method further comprises quantifying an amount of the target nucleic acid.

In another aspect, the invention provides a method for detecting the presence of a target nucleic acid, comprising: providing a first monomer and a second monomer to a solution comprising the target nucleic acid, each of the first and second monomers formed from an X-shaped nucleic acid and one or more Y-shaped nucleic acids, wherein the first monomer links to the second monomer with the aid of the target nucleic acid to form a dimer; and polymerizing the dimer to form a polymer.

In some embodiments, the first and/or second monomers comprise a Y-shaped nucleic acid having a crosslinkable moiety. In some embodiments, the crosslinkable moiety includes a photoreactive group. In some embodiments of the method, polymerizing the dimer comprises photo-polymerizing the dimer, e.g., via the photoreactive group.

In some embodiments, the first and/or second monomer comprises a Y-shaped nucleic acid having a functional moiety. The functional moiety can be, without limitation, a DNA capture probe, a fluorescent dye, a quantum dot, a gold nanoparticle, a peptide, a polypeptide, a protein, a lipid, a carbohydrate, an aptamer, an antibody, an antigen, a cell growth factor, a DNA binding agent, a detectable label, a selectable marker, biotin, a biologically active agent, a pharmaceutical agent, a drug, a small molecule, a therapeutic agent, a receptor molecule, a ligand, a nucleic acid molecule or a substrate.

In some embodiments, the method further comprises detecting the presence of the polymer. Detecting the presence of the polymer can comprise detecting the presence of one or more functional moieties of one or both of the first and second monomers. For example, detecting the presence of the polymer may comprise detecting fluorescent light emitted by a fluorescent dye linked to one or more monomers.

In some embodiments of the invention, the first monomer links to the second monomer via hybridization of the target nucleic acid with the first and second monomers. For example, the target nucleic acid can comprise a sequence that is complementary to a linking sequence of the first monomer and complementary to a linking sequence of the second monomer. The target can be a nucleic acid indicative of a condition, e.g, the presence of a pathogenic organism, disease state or environmental contaminant. The complementary sequence of the monomer can be designed to specifically hybridize to the target and to avoid hybridization to background nucleic acids, e.g., uninformative cellular DNAs or mRNAs, or nucleic acids of the composition. In some embodiments, the target nucleic acid comprises at least a portion of a pathogen nucleic acid.

In some embodiments, both of the first and second monomers are formed from an X-shaped nucleic acid and a plurality of Y-shaped nucleic acids. The plurality of Y-shaped nucleic acids may comprise, e.g., 2, 3 or 4 Y-shaped nucleic acids.

In some embodiments, both of the first and second monomers are formed by hybridizing an acceptor sequence of an X-shaped nucleic acid with a donor sequence of a Y-shaped nucleic acid. The X-shaped nucleic acid can be hybridized to the Y-shaped nucleic acid with the aid of a bridge DNA having a sequence complementary to the donor sequence of the Y-shaped nucleic acid and the acceptor sequence of the X-shaped nucleic acid.

Polymerizing the dimer according to the methods of the invention may comprise exposing a plurality of the dimers to electromagnetic radiation. The electromagnetic radiation can include without limitation ultraviolet (UV) light, visible light, near infrared, infrared, microwaves, gamma rays, X-rays, or radio waves.

In some embodiments of the methods of the invention, the nucleic acids, e.g., the X-shaped and Y-shaped nucleic acid, comprise deoxyribonucleic acid (DNA), ribonucleic acid (RNA), peptide nucleic acid (PNA), or combinations thereof.

In another aspect, the invention provides a composition comprising a first dimer comprising a first monomer and a second monomer, each of the first and second monomers comprising an X-shaped nucleic acid that is linked to one or more Y-shaped nucleic acids, the first monomer comprising a Y-shaped nucleic acid that is linked to a Y-shaped nucleic acid of the second monomer via a complementary linker, wherein the complementary linker is configured to be recognized by a target cell. The composition may further comprise a second dimer comprising a third monomer and a fourth monomer, each of the third and fourth monomers comprising an X-shaped nucleic acid that is linked to one or more Y-shaped nucleic acids, the third monomer comprising a Y-shaped nucleic acid that is linked to a Y-shaped nucleic acid of the fourth monomer, the third monomer comprising one or more Y-shaped nucleic acids hybridized to a nucleic acid sequence that is configured to be recognized by a target cell.

The X-shaped and Y-shaped nucleic acids of the composition may comprise deoxyribonucleic acid (DNA), ribonucleic acid (RNA), peptide nucleic acid (PNA), or a combination thereof.

In some embodiments, a Y-shaped nucleic acid of the first dimer is crosslinked to a Y-shaped nucleic acid of the second dimer. In some embodiments, the first, second, third and/or fourth monomers comprise two, three or four Y-shaped nucleic acids linked to one X-shaped nucleic acid.

In some embodiments, the one or more X-shaped or Y-shaped nucleic acids comprise a functional moiety. The functional moiety can be without limitation a DNA capture probe, a fluorescent dye, a quantum dot, a gold nanoparticle, a peptide, a polypeptide, a protein, a lipid, a carbohydrate, an aptamer, an antibody, an antigen, a cell growth factor, a DNA binding agent, a detectable label, a selectable marker, biotin, a biologically active agent, a pharmaceutical agent, a drug, a small molecule, a therapeutic agent, a receptor molecule, a ligand, a nucleic acid molecule or a substrate. In some embodiments, the nucleic acid sequences comprise a sequence encoding a small interfering ribonucleic acid (RNA).

In some embodiments, the complementary linker has a sequence that is complementary to a linker sequence of a Y-shaped nucleic acid of each of the first and second monomers. The complementary linker can comprise an oligonucleotide. In some embodiments, a Y-shaped nucleic acid of the first monomer is linked to an X-shaped nucleic acid of the first monomer via a bridge DNA having a sequence that is complementary to a donor sequence of the Y-shaped nucleic acid and an acceptor sequence of the X-shaped nucleic acid.

In some embodiments, the composition comprises a polymerized sphere.

In another aspect, the invention provides a method for delivering a therapeutic agent to a subject in need thereof, comprising administering the composition of the invention the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features of the present invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 illustrates photo-polymerization and characterization of ABC monomers, in accordance with an embodiment of the invention. FIG. 2B illustrates atomic force microscopy (AFM) image of polymeric spheres (higher magnification in the inset). Scale bar, 1 mm. FIG. 2C illustrates size distribution of polymeric spheres obtained using dynamic light scattering measurements. FIG. 2D illustrates right-field optical microscopy images after photo-crosslinking FIG. 2E illustrates overlay image obtained using both bright-field and fluorescence microscopy. Error bars represent standard deviations from three replicates. Scale bar, 5 mm (inset, 2 mm);

FIG. 6 illustrates ABC monomers with precisely positioned fluorescence dyes and nanoparticles, in accordance with an embodiment of the invention. FIG. 6A illustrates gel electrophoresis image of three donor Y-DNAs conjugated with one green fluorescence dye (1), two red fluorescence dyes (2,2), and one green and one red fluorescence dye (1,2). FIG. 6B illustrates gel electrophoresis image of ABC monomers with different configurations.

FIG. 9A illustrates a schematic drawing of ABC monomer synthesis with nanoparticles, in accordance with an embodiment of the invention. FIG. 9B illustrates microsphere beads labeled with 3 are observed by digital camera, in accordance with an embodiment of the invention. FIG. 9C shows that after isolation of 4 by restriction enzyme, the entire solution emits fluorescence indicating that ABC monomers are separated from the beads, in accordance with an embodiment of the invention;

FIG. 10A illustrates the distance between two QDs calculated by considering a rigid DNA model with 0.34 nm per base pair, in accordance with an embodiment of the invention. FIG. 10B illustrates the yield of ABC monomers anchoring three QDs are evaluated by STEM images, in accordance with an embodiment of the invention;

FIG. 11A illustrates fluorescence spectrum of individual green QDs and red QDs as the reference, in accordance with an embodiment of the invention. FIG. 11B is a fluorescence spectrum of synthesized 1G1R ABC monomers, in accordance with an embodiment of the invention;

FIG. 12 is a table with oligonucleotide sequences of pathogen DNA and DNA building blocks for target-driven polymerization, in accordance with an embodiment of the invention (SEQ ID NOS 1-17, respectively, in order of appearance);

FIG. 13 illustrates detection of pathogen DNA by means of target-driven polymerization of ABC monomers, in accordance with an embodiment of the invention. FIG. 13A-C illustrate fluorescence microscopic images of target-driven polymers with pathogen DNAs including SARS, *Bacillus anthracis* and Ebola, respectively, in accordance with an embodiment of the invention. FIG. 13D shows that by incubating 1G1R ABC monomers with an unrelated pathogen DNA, no polymerized DNA materials were observed, in accordance with an embodiment of the invention. Scale bars, 5 mm. FIG. 13E illustrates the relationship between the number of polymerized spheres per 140×180 mm2 and the concentration of pathogen DNA (for determining the sensitivity of detection through target-driven polymerization), in accordance with an embodiment of the invention. The coefficient of variation (CV) of the assay ranged from 5.6 to 10.4%, depending on the concentration of the target pathogen DNA. Error bars represent standard deviations from three replicates;

FIG. 14 illustrates microscopic images of a HeLa cell treated with polymeric spheres at 37° C. overnight and cytotoxicity studies, in accordance with an embodiment of the invention. FIGS. 14A-B illustrate fluorescence microscopy images (polymeric spheres have been indicated by arrows), in accordance with an embodiment of the invention. Scale bars, 10 mm. FIG. 14C illustrates confocal microscopy image with re-sliced regions of interest, in accordance with an embodiment of the invention. FIG. 14D illustrates cytotoxicity studies of polymeric spheres, in accordance with an embodiment of the invention. The assay shows cytotoxicity after 36 h exposures of cells to 0.01, 0.05, 0.25, 1 and 5 nM ABC monomers. Error bars represent standard deviations from three replicates;

FIG. 15 illustrates fluorescence microscopic images of HeLa cell treated with polymeric spheres, in accordance with an embodiment of the invention (darker cells are disposed within lighter actin). FIG. 15A illustrates at 4° C. overnight; FIG. 15B illustrates at 37° C. for 10 min. Scale bar is 10 μm, in accordance with an embodiment of the invention;

FIG. 18 illustrates dynamic light scattering data of the ABC monomers and polymeric spheres, in accordance with an embodiment of the invention. FIG. 18A illustrates the increase of size of the polymeric spheres after photo-polymerization, in accordance with an embodiment of the invention. FIG. 18B illustrates changes of polymeric sphere sizes with different concentrations of ABC monomers, in accordance with an embodiment of the invention;

FIG. 19 is a table with oligonucleotide sequences of the DNA building blocks for ABC monomers with fluorescent dyes, in accordance with an embodiment of the invention (SEQ ID NOS 18-35, respectively, in order of appearance);

FIG. 20 is a table with oligonucleotide sequences of the DNA building blocks for ABC monomers with nanoparticles, in accordance with an embodiment of the invention (SEQ ID NOS 36-49, respectively, in order of appearance); and FIG. 21 is a table with pre-assigned fluorescence code library of nano-architectures, in accordance with an embodiment of the invention. To experimentally decode the color signal of polymeric spheres, the signal intensity is counted as photon counts per pixel area with a pixel in the microscope image.

DETAILED DESCRIPTION

Figure 1:
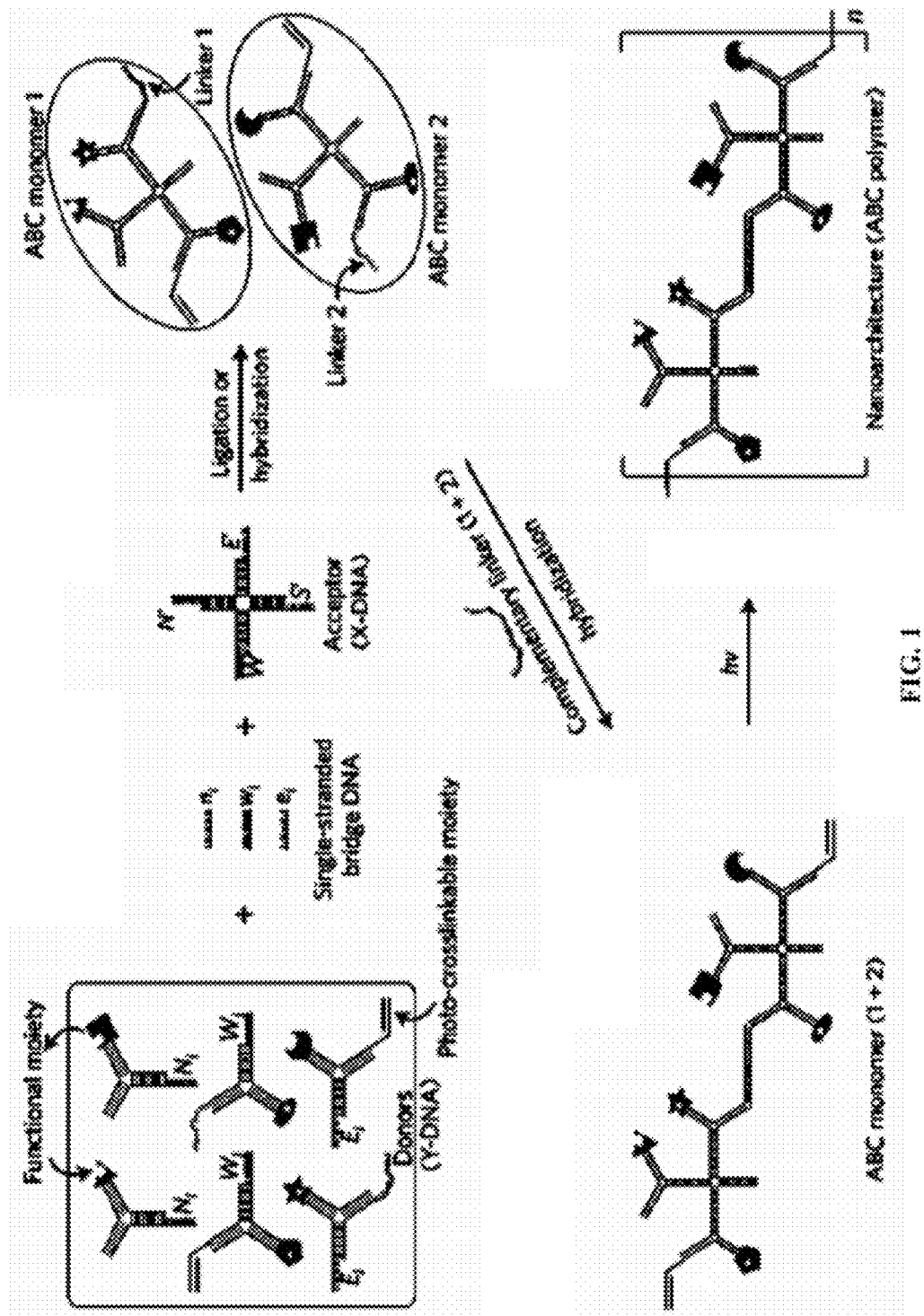
FIG. 1 is a schematic illustration of the assembly of an ABC monomer (also "monomer" herein) and target-driven photo-polymerization, in accordance with an embodiment of the invention.

While various embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

In embodiments, nucleic acid molecules, such as the building blocks of monomers, can be branched nucleic acids that are X-, Y-, T-, or dumbbell shaped (collectively referred to as "multimers" or a "multimer"). Branched nucleic acid molecules can also be dendrimer-like, can form dendrimers and can be referred to as dendrimer-like nucleic acid molecules ("DL-NAMs"). A solution comprising branched nucleic acid molecules can include two or more different-shaped multimers, wherein the ratio of one multimer to another multimer can be selected as desired. The nucleic acids can comprise deoxyribonucleic acid (DNA), ribonucleic acid (RNA), peptide nucleic acid (PNA), or a combination thereof. The branched nucleic acid molecules can comprise oligonucleotides. The nucleic acid molecules can comprise coding and non-coding nucleic acid molecules.

The practice of various embodiments of the invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The terms "polynucleotide", "nucleotide", "nucleotide sequence", "nucleic acid", "nucleic acid molecule", "nucleic acid sequence," and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. For example, oligonucleotides can be oligodeoxynucleotides. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. Small interfering RNA (siRNA), sometimes known as short interfering RNA or silencing RNA, are typically double-stranded RNA molecules of 20-25 nucleotides in length. siRNA can interfere with the expression of certain genes. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability. miRNAs are single-stranded RNA molecules of 21-23 nucleotides in length. miRNAs are typically partially complementary to one or more messenger RNA (mRNA) molecules, and hybridize thereto to down-regulate gene expression. Small nuclear RNA (snRNA) is a class of small RNA molecules that are found within the nucleus of eukaryotic cells. snRNA are involved in a variety of biological processes such as RNA splicing, regulation of transcription factors (7SK RNA) or RNA polymerase II (B2 RNA), and maintaining telomeres. They associate with specific proteins, and the complexes are referred to as small nuclear ribonucleoproteins (snRNP) or "snurps."

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components.

A polynucleotide may be further modified after polymerization, such as by conjugation with a labeling component. The nucleic acids, used in the various embodiments disclosed herein, may be modified in a variety of ways, including by crosslinking, intra-chain modifications such as methylation and capping, and by copolymerization. Additionally, other beneficial molecules may be attached to the nucleic acid chains. For example, photo-crosslinkable moeities can be attached to the nucleic acid chains. The nucleic acids may have naturally occurring sequences or artificial sequences. The sequence of the nucleic acid may be irrelevant for many aspects disclosed herein. However, special sequences may be used to prevent any significant effects due to the information coding properties of nucleic acids, to elicit particular cellular responses or to govern the physical structure of the molecule.

In embodiments, the nucleic acids for use with the invention comprise deoxyribonucleic acid (DNA). Y-shaped DNA can be referred to as "Y-DNA" or "Y DNA"; Y-shaped RNA can be referred to as "Y-RNA" or "Y RNA"; X-shaped DNA can be referred to as "X-DNA" or "X DNA"; and X-shaped RNA can be referred to as "X-RNA" or "X RNA". X-shaped nucleic acids and Y-shaped nucleic acids have been described in U.S. patent application Ser. No. 11/464,181 ("NUCLEIC ACID-BASED MATRIXES") to Luo et al., U.S. patent application Ser. No. 11/464,184 ("NUCLEIC ACID-BASED MATRIXES FOR PROTEIN PRODUCTION") to Luo et al., U.S. patent application Ser. No. 11/423,633 ("DETECTION OF TARGET MOLECULES WITH LABELED NUCLEIC ACID DETECTION MOLECULES") to Luo et al., each of which are entirely incorporated herein by reference in their entirety. Methods of linking nucleic acid via photocrosslinking are presented in PCT Patent Application PCT/US2009/52795, filed Aug. 5, 2009 and entitled "PHOTO-CROSSLINKING-BASED METHOD FOR CREATING DNA HYDROGELS," which is incorporated herein by reference in its entirety. Methods for forming X-shaped nucleic acid and Y-shaped nucleic acid are described in, e.g., Li, Y., Tseng, Y. D., Kwon, S. Y., D'Espaux, L., Bunch, J. S., McEuen, P. L., Luo, D., Nat. Mater. 3, 38-42 (2004), Li, Y., Cu, Y. T., Luo, D. Nat. Biotechnol. 23, 885-889 (2005), Um, S. H., Lee, J. B., Park, N., Kwon, S. Y., Umbach, C. C., Luo, D. Nat. Mater. 5, 797-801 (2006) and Lee, J. B., Roh, Y. H, Um, S. H., Funabashi, H., Cheng, W., Cha, J. J., Kiatwuthinon, P., Muller, D. A., and Luo, D., Nat. Nanotechnol. 4 (7), 430-436 (2009) (including supplemental information, pg. 1-14) (collectively "the Luo publications" herein), which are entirely incorporated herein by reference.

In embodiments of the invention, methods and systems are provided for the creation of anisotropic, branched and crosslinkable building blocks (also "ABC monomers" herein) from which multifunctional nano-architectures can be assembled. In various embodiments, target-driven polymerization processes are provided in which polymers can be generated only in the presence of a specific nucleic acid (e.g., DNA, RNA) molecule, leading to highly sensitive pathogen detection. In various embodiments, using this monomer system, a biocompatible nanovector is provided that can deliver, e.g., biologically active agents and tracers. Methods of embodiments of the invention can provide a general, yet versatile, route towards the creation of a range of multifunctional nano-architectures.

As used herein, the terms "biologically active agent" or "bioactive agent" are used interchangeably and include but are not limited to a biological or chemical compound such as a simple or complex organic or inorganic molecule, peptide, peptide mimetic, protein (e.g. antibody, angiogenic, anti-angiogenic and cellular growth factors), an antigen or immunogen, liposome, small interfering RNA (siRNA), or a polynucleotide (e.g. vector, virus, viral vector, or anti-sense), therapeutic agents, organic or inorganic molecules can include a homogenous or heterogeneous mixture of compounds, including pharmaceuticals, radioisotopes, crude or purified plant extracts, and/or a cell, entities that alter, inhibit, activate, or otherwise affect biological or biochemical events, including classes of molecules (e.g., proteins, amino acids, peptides, polynucleotides, nucleotides, carbohydrates, sugars, lipids, nucleoproteins, glycoproteins, lipoproteins, steroids, growth factors, chemoattractants, aptamers, etc.) that are commonly found in cells and tissues, whether the molecules themselves are naturally-occurring or artificially created (e.g., by synthetic or recombinant methods). Such agents may be naturally derived or synthetic. "Therapeutic agents" include molecules or atoms which are useful for therapy. Examples of therapeutic agents include drugs, toxins, immunomodulators, chelators, antibodies, antibody-drug conjugates, photoactive agents or dyes, and radioisotopes.

Examples of such agents include but are not limited to drugs, for example, small molecules, anti-cancer substances, analgesics, opioids, anti-AIDS substances, anti-cancer substances, immunosuppressants (e.g., cyclosporine), anti-viral agents, enzyme inhibitors, neurotoxins, hypnotics, anti-histamines, lubricants, tranquilizers, anti-convulsants, muscle relaxants and anti-Parkinson agents, anti-spasmodics and muscle contractants including channel blockers, miotics and anti-cholinergics, anti-glaucoma compounds, anti-parasite, anti-protozoal, and/or anti-fungal compounds, modulators of cell-extracellular matrix interactions including cell growth inhibitors and anti-adhesion molecules, vasodilating agents, inhibitors of DNA, RNA or protein synthesis, anti-hypertensives, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, targeting agents, neurotransmitters, proteins, cell response modifiers, and vaccines.

In some embodiments, a drug for use with the invention has been deemed safe and effective for use by the appropriate governmental agency or body. For example, drugs for human use listed by the United States Food and Drug Administration (FDA) under 21 C.F.R. §§330.5, 331 through 361, and 440 through 460; drugs for veterinary use listed by the FDA under 21 C.F.R. §§500 through 589, incorporated herein by reference are all considered acceptable for use in accordance with compostions and methods disclosed herein.

In various embodiments, branched nucleic acid molecules are provided that can be X-, Y-, T-, dumbbell-, dendrimer-shape or any combination thereof. In other embodiments, branched and linear nucleic acid molecules are provided, where the branched nucleic acid molecules can be X-, Y-, T-, dumbbell-, dendrimer-shape or any combination thereof. Multimers, such as, e.g., dimers, formed according to methods of embodiments of the invention can be entirely comprised of DNA, DNA and RNA, or entirely RNA. In an embodiment, dimers can be comprised of DNA and not RNA.

In another embodiment, dimers can be comprised of RNA but not DNA. In yet another embodiment, dimers can be comprised of DNA and RNA. In some embodiments, multimers can be comprised of TNA, PNA and LPNA, including a combination of any such nucleic acids, as well analogs thereof.

In embodiments of the invention, building blocks are provided for creating nano-structures and nano-architectures. The nano-structure can be anisotropic, branched, crosslinkable (also "cross-linkable" herein), or any combination thereof. In embodiments, building blocks are provided for creating structures that are multifunctional. In some embodiments, building blocks are provided that are synergistically multifunctional. The nano-structures can be multifunctional. In some embodiments, the functionalities of a nano-structure can be synergistic.

Nano-structures can be obtained by assembling different moieties onto a core building block leading to applications in nanoelectronics, nanophotonics, intelligent sensing, pathogen detection and drug delivery. A nano-structure can be assembled by attaching different moieties onto a building block, such as a core block. The core block can be multivalent, anisotropic, or both. In some embodiments, an anisotropic, branched, and crosslinkable building blocks, such as an ABC monomer, can be used to assemble a multifunctional nano-architecture. Polymerization of building blocks can be used to form the nano-structures. The polymerization can be target-driven, such as by synthesizing polymers in the presence of a specific DNA, leading to sensitive pathogen sensing. In some embodiments, the nano-structure can be a biocompatible multi-drug delivery vector that delivered drugs and tracers together.

The nano-structures can be formed using a modular ("plug-and-play") approach. For example, an ABC monomer can be first created and then a nano-structure, such as a multifunctional nano-architecture, can be developed from the ABC monomer. In embodiments, an ABC monomer can be used to form an ABC trimer. In some embodiments, an ABC monomer (also "monomer" herein) can be used to form an ABC dimer (also "dimer" herein). In other embodiments, a monomer can be used to form an ABC trimer (also "trimer" herein). The ABC dimer can be used to generate a nucleic acid-containing polymer. In preferable embodiments, a multimer (e.g., dimer) forms with the aid of a nucleic acid linker, such as a nucleic acid sequence that is partially complementary to portions of monomers used to form the multimer. The nucleic acid linker can be a target nucleic acid. In a preferable embodiment, an ABC dimer forms in the presence of a target nucleic acid, such as a nucleic acid sequence that is partially complementary to portions of monomers.

In various embodiments, multimers can comprise different monomers. In some embodiments, multimers can comprise the same monomer. For example, a dimer can comprise different monomers. As another example, a dimer can comprise the same monomer.

In some embodiments, at least a portion of the nucleic acid molecules used with the invention are linked to one or more additional compounds, e.g., compounds comprising functional moieties. For example, the functional moieties can be linked by covalent or non-covalent attachment to X-shaped nucleic acids, Y-shaped nucleic acids, or other nucleic acids of the monomers. Non-limiting examples of the one or more additional compounds include a peptide, a polypeptide, a protein, a lipid, a carbohydrate, an aptamer, an antibody, an antigen, a cell growth factor, a DNA binding agent, a detectable label, a selectable marker, biotin, a pharmaceutical agent, a drug, a small molecule, a therapeutic agent, a receptor molecule, a ligand, a nucleic acid molecule or a substrate. In some embodiments, the other biological molecules are also photo-crosslinked to the nucleic acids. The nucleic acids can also be linked, e.g., via photo-crosslinks, with one or more polymers.

Non-limiting examples of useful polymers include poly(ethylene glycol) (PEG), poly(N-isopropylacrylamide), poly(N-alkylacrylamide), poly(N-n-propylacrylamide), poly(N-isopropylmethacrylamide), a peptide, a polypeptide, poly(ethylene oxide)-poly(propylene oxide)-poly(ethylene oxide), poly(DTEC), dextran-polylactide, elastin-like polypeptides, a polyester, polylactide, poly(L-lactic acid), poly(D,L-lactic acid), poly(lactide-co-glycolides), biotinylated poly(ethylene glycol-block-lactic acid), poly(alkylcyanoacrylate), poly(epsilon-caprolactone), polyanhydride, poly(bis(p-carboxyphenoxy)propane-sebacic acid), poly-orthoester, polyphosphoester, polyphosphazene, polystyrene, polyurethane, poly(amino acid), poly(ethylene oxide), poly(ethylene oxide)-polypropylene-poly(ethylene oxide), poly(lactic acid)-g-poly(vinyl alcohol), poly(ethylene oxide)-poly(L-lactic acid), poly(D,L-lactic-co-glycolic acid)-poly(ethylene glycol), poly(L-lactide-ethylene glycol), poly(ethylene glycol)-co-poly(hydroxyl Acid), poly(vinyl alcohol), poly(lactic acid-co-lysine)-poly(aspartic acid), poly(-caprolactone-co-trimethylene carbonate), poly(L-lactic acid-co-glycolic acid-co-L-serine), poly(propylene fumarate), oligo(poly(ethylene glycol) fumarate), poly(propylene furmarate-co-ethylene glycol), poly(ethylene glycol) di[ethylphosphatidyl(ethylene glycol)methacrylate], poly(N-isopropylacrylamide)-poly(ethylene glycol), poly(N-isopropylacrylamide)-gelatin, poly(N-isopropylacrylamide-acrylic acid) or a derivative of any thereof. The nucleic acids can also be linked, e.g., via photo-crosslinks, with one or more polymers. Non-limiting examples of useful polymers poly(ethylene glycol) (PEG), poly(N-isopropylacrylamide), poly(N-alkylacrylamide), poly(N-n-propylacrylamide), poly(N-isopropylmethacrylamide), a peptide, a polypeptide, poly(ethylene oxide)-poly(propylene oxide)-poly(ethylene oxide), poly(DTEC), dextran-polylactide, elastin-like polypeptides, a polyester, polylactide, poly(L-lactic acid), poly(D,L-lactic acid), poly(lactide-co-glycolides), biotinylated poly(ethylene glycol-block-lactic acid), poly(alkylcyanoacrylate), poly(epsilon-caprolactone), polyanhydride, poly(bis(p-carboxyphenoxy)propane-sebacic acid), poly-orthoester, polyphosphoester, polyphosphazene, polystyrene, polyurethane, poly(amino acid), poly(ethylene oxide), poly(ethylene oxide)-polypropylene-poly(ethylene oxide), poly(lactic acid)-g-poly(vinyl alcohol), poly(ethylene oxide)-poly(L-lactic acid), poly(D,L-lactic-co-glycolic acid)-poly(ethylene glycol), poly(L-lactide-ethylene glycol), poly(ethylene glycol)-co-poly(hydroxyl Acid), poly(vinyl alcohol), poly(lactic acid-co-lysine)-poly(aspartic acid), poly(-caprolactone-co-trimethylene carbonate), poly(L-lactic acid-co-glycolic acid-co-L-serine), poly(propylene fumarate), oligo(poly(ethylene glycol) fumarate), poly(propylene furmarate-co-ethylene glycol), poly(ethylene glycol) di[ethylphosphatidyl(ethylene glycol)methacrylate], poly(N-isopropylacrylamide)-poly(ethylene glycol), poly(N-isopropylacrylamide)-gelatin, poly(N-isopropylacrylamide-acrylic acid) or a derivative of any thereof.

In some embodiments of the invention, the nucleic acids are linked to a detectable label, e.g., to facilitate detection of a pathogen or other target cell. Detectable labels for use with the invention include a radiolabeled probe, a fluorophore-labeled probe, a quantum dot-labeled probe, a chromophore-labeled probe, an enzyme-labeled probe, an affinity ligand-labeled probe, an electromagnetic spin labeled probe, a heavy atom labeled probe, or a nanoparticle light scattering labeled probe. In some embodiments, the detectable label comprises a chromophore, a fluorescent moiety, an enzyme, an antigen, a heavy metal, a magnetic probe, a dye, a nanocrystal, a phosphorescent group, a radioactive material, a chemiluminescent moiety, a scattering nanoparticle, a fluorescent nanoparticle, a Raman signal generating moiety, or an electrochemical detection moiety. In some embodiments, the detectable label comprises horseradish peroxidase, alkaline phosphatase, β-galactosidase, acetylcholinesterase, streptavidin, avidin, biotin, an aptamer, an antigen, an antibody, an immunoglobulin, an anti-immunoglobulin, umbelliferone, fluorescein, fluorescein isothiocyanate (FITC), rhodamine, tetramethyl rhodamine, TRITC, eosin, green fluorescent protein, erythrosin, coumarin, methyl coumarin, pyrene, malachite green, stilbene, lucifer yellow, Cascade Blue™, Texas Red, Phar-Red, allophycocyanin (APC), dichlorotriazinylamine fluorescein, dansyl chloride, R-phycoerythrin, phycoerythrin, a fluorescent lanthanide complex, Europium, Terbium, Cy3, Cy5, Cy7, digoxigenin, dinitrophenyl, a molecular beacon, a fluorescent molecular beacon derivative, luminol, a light scattering material, a plasmon resonant material, gold, silver, a quantum dot, $^{14}C$, $^{123}I$, $^{124}I$, $^{125}I$, $^{131}I$, Technetium-99m ($^{Tc}99m$), $^{35}S$, $^{32}P$ or $^{3}H$. The detectable label can be used as a tracer.

In some embodiments, at least a portion of the nucleic acid molecules of the compositions of the invention comprise a photoreactive group, e.g., conjugated to their 5'-end, 3'-end, or internally. A group conjugated internally refers to a group that is not bound to either the 5' or 3' end of the nucleic acid molecule. In some embodiments, the nucleic acids are conjugated to a photoreactive group at more than one location. In these embodiments, the photoreactive groups can all be the same group or can differ, even within one nucleic acid molecule. The branched chain nucleic acid molecules can comprise any relevant form of nucleic acids, e.g., deoxyribonucleic acid (DNA), ribonucleic acid (RNA), peptide nucleic acid (PNA), or a combination thereof. In some embodiments, the plurality of branched nucleic acid molecules comprises oligonucleotides.

In some embodiments, the photoreactive group comprises a vinyl, acrylate, N-hydroxysuccinimide, amine, carboxylate or thiol moiety. In some embodiments, the photoreactive group is a primary amine modified group, a secondary amine modified group, or a tertiary amine modified group. The photocrosslinking step can be performed under electromagnetic radiation, e.g., in the visible, ultraviolet (UV), near infrared, infrared, and/or microwave regions. Photo-reactive amino acid analogs include photoreactive diazirine analogs to leucine and methionine. L-Photo-Leucine and L-Photo-Methionine are analogs of the naturally occurring L-Leucine and L-Methionine amino acids and can form crosslinks when exposed to UV light. The photocrosslinking can also be performed using gamma rays, X-rays, or radio waves as appropriate. The photocrosslinking can also be performed using a crosslinker, e.g., a UV crosslinker.

In some embodiments, the photocrosslinking is performed in the presence of a photoinitiator, including but not limited to Irgacure. A photoinitiator typically includes an agent that forms free radicals when illuminated by light of appropriate wavelengths. For example, Igracure from CIBA is a photoinitiator for radical polymerization upon light exposure. Non-limiting example classes of compounds useful as photoinitiators include aromatic carbonyl compounds (e.g., benzoin derivatives, benziketals, acetophenone derivatives, hydroxyalkylphenones) and aromatic ketones (e.g., benzophenone and thioxanthone). Non-limiting examples of photoinitiators include Esacure from Lamberti spa, benzophenone, dimethoxyphenyl acetophenone, 2,2-dimethoxy, 2-phenylacetophenone and 2,2-diethoxyacetophenone, 1-[4-(2-hydroxyethoxy)-phenyl]-2-hydroxy-2-methyl-1-propane-1-one, ethyl eosin, eosin Y, fluorescein, 2,2-dimethoxy, 2-phenylacetophenone, 2-methyl, 2-phenylacetonphenone, I2959, camphorquinone, rose bengal, methylene blue, erythosin, phloxime, thionine, riboflavin, and methyl green. Other photoinitiators are listed and described in U.S. Pat. Nos. 3,715,293 and 3,801,329. Still other photoinitiators comprise 1-(4-Fluorphenyl)-2-methyl-2-morpholino-1-propanone, 1,7-bis(9-acridinyl)heptane, 1-Chloro-4-propoxythioxanthone, 1-Hydroxy cyclohexyl phenyl ketone, 2,2-Di ethoxy acetophenone, 2,3,4,4'-Tetrahydroxy Benzophenone, 2,3,4-Trihydroxybenzophenone, 2,4,6-Trimethyl benzoyl diphenyl phosphine oxide, 2,4,6-Trimethylbenzophenone, 2/4-Diethylthioxanthone, 2/4-Isopropylthioxanthone, 2-Benzyl-2-(dimethylamino)-1-[4-(4-morpholinyl)phenyl]-1-butanone, 2-Chlorothioxanthone, 2-Dimethyl-aminoethylbenzoate, 2-Ethylhexyl-4-dimethylaminobenzoate, 2-Hydroxy-2-methyl-phenyl-propan-1-one, 2-Hydroxy-4'-hydroxyethoxy-2-methylpropiophenone, 2-Isopropylthioxanthone, 2-Methyl Benzophenone, 2-Methyl-1-[4-(methylthio)phenyl]-2-morpholinopropanone-1,4-(4-Methylphenylthiophenyl)-phenylmethanone, 4,4'-Difluoro benzophenone, 4,4'-Dimethoxy benzophenone, 4-Chloro benzophenone, 4-Methyl acetophenone, 4-Methyl benzophenone, 4-Phenylbenzophenone, Benzil dimethyl ketal, Benzophenone, Benzophenone hydrazone, Bis(p-tolyl) iodonium hexafluorophosphate, Dimethyl Sebacate, Diphenyl Iodonium Hexafluorophosphate, Ethyl (2,4,6-trimethylbenzoyl) phenylphosphinate, Ethyl-4-(dimethylamino) benzoate, Methyl o-benzoyl benzoate, Methyl phenyl glyoxylate, N,N,N',N'-Tetraethyl-4,4-diaminobenzophenone, Phenyltribromomethylsulphone, acylphosphine oxide (APO) and bisacylphosphine oxide (BAPO), 1-[4-(2-Hydroxyethoxy)-phenyl]-2-hydroxy-2-methyl-1-propane-1-one, 2,2-Dimethoxy-1,2-diphenylethan-1-one, hydroxy-cyclohexyl-phenyl-ketone, methylbenzoylformate, oxy-phenyl-acetic acid 2-[2 oxo-2 phenyl-acetoxy-ethoxy]-ethyl ester, oxy-phenyl-acetic 2-[2-hydroxy-ethoxy]-ethyl ester, alpha-dimethoxy-alpha-phenylacetophenone, 2-Benzyl-2-(dimethylamino)-1-[4-(4-morpholinyl)phenyl]-1-butanone, diphenyl (2,4,6-trimethylbenzoyl)-phosphine oxide, phosphine oxide, bis(eta 5-2,4-cyclopentadien-1-yl), bis[2,6-difluoro-3-(1H-pyrrol-1-yl)phenyl]titanium, Iodonium, (4-methylphenyl)[4-(2-methylpropyl)phenyl]-hexafluorophosphate(1-), bis(2,6-dimethoxybenzoyl)-2,4,4-trimethyl pentylphosphineoxide. Photoinitiators also comprise related compounds and derivatives of these compounds.

A "target molecule," "target nucleic acid," or "target" includes a molecule, e.g., a nucleic acid, specifically bound by a nucleic acid binding agent according to the invention, e.g., by the hybridization of complementary nucleic acids. The target can be a polynucleotide to be detected. For example, the target may be indicative of a condition. The condition may comprise a disease state, the presence of a DNA or RNA from a pathogen foreign to a host cell or host organism. The target can also be derived from a host cell or host organism itself. For example, the target may be an mRNA that is differentially expressed, i.e., overexpressed or underexpressed, in a diseased cell versus a corresponding non-diseased cell. Such differential expression may occur, e.g., in a virally infected or cancer cell. The target may also comprise a gene segment, intron, exon, genomic DNA or chromosomal DNA. In some embodiments, the target comprises a stretch of genomic DNA or chromosome that is present in certain disease states, e.g., a break or fusion that occurs in a cancer cell. Detecting the fusion can be used to detect the diseased cell, thereby providing a means for diagnosis or theranosis. In a non-limiting example, the target molecule comprises a pathogen nucleic acid that hybridizes to a nucleic acid of a composition of the invention. The target could also be an environmental target, e.g., a polynucleotide from a microorganism that is indicative of contaminated water, food, soil, or other environmental sample. One of skill in the art will recognize that the compositions and methods of the invention can be used to detect the presence or absence of the target, thereby detecting the presence or absence of a disease state, environmental contaminant, etc.

Non-limiting examples of targets include a biowarfare agent, biohazardous agent, infectious agent, virus, bacterium, *Salmonella*, *Streptococcus*, *Legionella*, *E. coli*, *Giardia*, *Cryptosporidium*, *Rickettsia*, spore, mold, yeast, algae, amoebae, dinoflagellate, unicellular organism, pathogen or cell. In certain embodiments, cells exhibiting a particular characteristic or disease state, such as a cancer cell, may be targets.

The nucleic acids of the invention can be targeted to hybridize to or recognize specific nucleic acid sequences, e.g., a genomic sequence of a target pathogen or host cell. The nucleic acids can be designed to be complementary to section of the target while avoiding hybridization to non-target DNA. For example, the nucleic acids used to form monomers of the invention can be designed to not hybridize with other monomers or branched nucleic acids of the invention. The following terms are used to describe the sequence relationships between two or more polynucleotides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a segment of or the entirety of a specified sequence.

As used herein, "comparison window" makes reference to a contiguous and specified segment of a polynucleotide sequence, wherein the polynucleotide sequence in the comparison window may include additions or deletions (i.e., gaps) compared to the reference sequence (which does not include additions or deletions) for optimal alignment of the two sequences. Generally, the comparison window is at least 5, 10, or 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty can be introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS*, 4:11 (1988), which is hereby incorporated by reference in its entirety; the local homology algorithm of Smith et al., *Adv. Appl. Math.*, 2:482 (1981), which is hereby incorporated by reference in its entirety; the homology alignment algorithm of Needleman and Wunsch, *JMB*, 48:443 (1970), which is hereby incorporated by reference in its entirety; the search-for-similarity-method of Pearson and Lipman, *Proc. Natl. Acad. Sci. USA*, 85:2444 (1988), which is hereby incorporated by reference in its entirety; the algorithm of Karlin and Altschul, *Proc. Natl. Acad. Sci. USA*, 87:2264 (1990), which is hereby incorporated by reference in its entirety; modified as in Karhn and Altschul, *Proc. Natl. Acad. Sci. USA*, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988), Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994), which are hereby incorporated by reference in their entirety. The ALIGN program is based on the algorithm of Myers and Miller, supra. The BLAST programs of Altschul et al., *JMB*, 215:403 (1990); *Nucl. Acids Res.*, 25:3389 (1990), which are hereby incorporated by reference in their entirety, are based on the algorithm of Karlin and Altschul supra.

Software for performing BLAST analyses is publicly available through the National Center for Biotechnology Information (worldwideweb.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res.* 25:3389 (1997), which is hereby incorporated by reference in its entirety. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See worldwideweb.ncbi.nlm.nih.gov. Alignment may also be performed manually by inspection.

Comparison of nucleotide sequences for determination of percent sequence identity to the sequences disclosed herein can be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and, therefore, do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide includes a sequence that has at least 51%, 52%, 53%, 54%, 55%, 56%, 57%, 58%, 59%, 60%, 61%, 62%, 63%, 64%, 65%, 66%, 67%, 68%, or 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

The term "hybridized" as applied to a polynucleotide refers to the ability of the polynucleotide to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

As is known to one skilled in the art, hybridization can be performed under conditions of varying stringency. Suitable hybridization conditions are such that the recognition interaction between the probe and target ER-stress related gene is both sufficiently specific and sufficiently stable. Conditions that increase the stringency of a hybridization reaction are widely known and published in the art. See, for example, (Sambrook, et al., (1989), supra; Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445, 934.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution.

For DNA-DNA hybrids, the $T_m$ can be approximated from the equation of Meinkoth and Wahl, *Anal. Biochem.*, 138:267 (1984), which is hereby incorporated by reference in its entirety; $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH.

However, severely stringent conditions can use a hybridization and/or wash at 1, 2, 3, or 4° C. lower than the thermal melting point ($T_m$); moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, Part I Chapter 2 "Overview of Principles of Hybridization and the Strategy of Nucleic Acid Probe Assays," Elsevier, New York (1993), which is hereby incorporated by reference in its entirety. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g. more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In other embodiments, purified nucleic acids may be linked to other nucleic acids or other compounds to reduce degradation. Linking may be accomplished in a variety of ways, including hydrogen bonds, ionic and covalent bonds, π-π bonds, polarization bonding, van der Waals forces. As used herein, "link" and "cross-link" are used interchangeably. More than one type of crosslinking may be used within a given biomaterial. For example, use of a type of crosslinking easily degraded in a cell coupled with a more degradation resistant type of crosslinking may result in a biomaterial that is opened in two phases, one when the easily degraded crosslinks are broken and second when the more resistant crosslinks or the nucleic acid itself are degraded. In some embodiments, crosslinking is accomplished by UV radiation, esterification, hydrolysis, intercalating agents, neoplastic agents, formaldehyde, formalin, or silica compounds. Such methods are taught by U.S. patent application Ser. No. 11/464,181, filed Aug. 11, 2006 and entitled "Nucleic Acid-Based Matrixes." Examples of linking include but are not limited to the use of siloxane bridges as described in U.S. Pat. No. 5,214,134. The present invention further provides photocrosslinking of the nucleic acids. In some embodiments, photoreactive groups are conjugated to the nucleic acids and linking occurs on exposure to light sufficient to link the photoreactive groups.

Crosslinking may occur between two strands of a double stranded nucleic acid or between the strands of two separate double strands. It may also occur between two separate single strands. Double strand to single strand crosslinking is also possible, as is crosslinking between different regions of one strand. Increased levels of crosslinking will generally slow degradation of nucleic acids. Linkers such as small organic molecules (esters, amines) or inorganic molecules (silicas, siloxanes), including microparticles or nanoparticles thereof, may be used to attach copolymers to nucleic acids. Any of the different shaped nucleic acids of the invention can be linked or cross-linked by one or methods described herein. Therefore, X-shaped, Y-shaped, T-shaped, dumbbell shaped or any combination thereof can be linked to each other, as well as to other chemical moieties or polymeric compounds.

In addition, in certain aspects, the nucleic acids can be linked to biologically active agents, including drugs, selection markers, detectable signals, other therapeutic agents, peptides, such as signal or cell targeting peptides, nucleic acid sequences, proteins (including antibodies), plasmids, viruses, viral vectors, small molecules, inorganic compounds, metals or derivatives thereof. Additionally, any inorganic or organic molecules, including amino acids, silicas, cytokines, such as interleukins, biologics and drugs may be added to the nucleic acid polymers to produce certain biological effects. Nucleic acids provide a variety of molecular attachment sites and therefore facilitate covalent, ionic and hydrogen bonding, as well as Van der Waals attachments, or other forms of attachment. In some embodiments, these molecules are also linked to nucleic acids by photo-crosslinking.

In one embodiment, a nucleic acid-based matrix is strengthened by cross-linking nanoparticles or microparticles onto the nucleic acids of the matrix. In one embodiment, the nucleic acids are branched DNA molecules. In some embodiments, the nanoparticles or microparticles are gold, silver, copper, iron, carbon black, 4-phosphonooxy-2,2,6,6-tetramethylpiperidyloxy nitr-oxide, titanium dioxide, and a magnetic material.

In addition, the nucleic acids may be methylated, ethylated, alkylated, or otherwise modified along the backbone to influence degradation rates. Generally, methylated, hemi-methylated, ethylated, or alkylated nucleic acids will degrade more slowly. Other backbone modifications affecting degradation rates include the use of heteroatomic oligonucleoside linkages as described in U.S. Pat. No. 5,677,437. Additionally, modifications may be used to prevent the nucleic acid from being transcribed or translated in a given tissue or organism. In addition, the nucleic acids may be capped to prevent degradation. Such caps are generally located at or near the termini of the nucleic acid chains. Examples of capping procedures are included in U.S. Pat. Nos. 5,245,022 and 5,567,810.

Target-Driven Polymerization

In an aspect of the invention, methods for detecting a target nucleic acid are provided. The target nucleic acids can comprise DNA, RNA, PNA or combinations thereof. The target nucleic acids can incorporate naturally occurring and non-natural nucleic acid monomers. In various embodiments, the target nucleic acids can be a pathogen nucleic acid. In embodiments, the target nucleic acid can be single or double stranded nucleic acids, such as single or double stranded DNA or RNA. In cases in which a double stranded nucleic acid is present, an enzyme (e.g., DNA helicases) can be used to unzip the double helix to provide single helixes.

Target-driven polymerization structures and methods of embodiments of the invention provide the capability to detect the presence of a known or unknown nucleic acid sequence (e.g., pathogen) in a sample or solution having the nucleic acid sequence.

In embodiments of the invention, methods for detecting a target nucleic acid molecule comprise subjecting a solution having nucleic acid-containing monomers (also "monomers" herein) and one or more nucleic acid strands to a stimulus capable of inducing a polymerization reaction between multimers formed from the nucleic acid-containing monomers and the target nucleic acid. In an embodiment, the multimers are dimers. In an embodiment, the stimulus is light, such as, e.g., ultraviolet ("UV") light or other electromagnetic radiation as described herein. In an embodiment, the stimulus can induce and/or facilitate cross-linking between the multimers to form a nucleic acid-containing polymer (also "polymeric material" herein).

Methods of preferable embodiments of the invention can be used to detect the presence of a nucleic acid molecule having a known or unknown nucleic acid sequence (also "sequence" herein), such as the nucleic acid sequence from an unknown pathogen. This can be achieved by providing monomers to a solution, the monomers having sequences complementary to a portion of a target nucleic acid molecule, and subjecting the solution to a stimulus (e.g., UV light) to induce polymerization. The presence of the target nucleic acid can then be determined by the presence of a polymer having multimers (e.g., dimers) formed from the target nucleic acid molecule—the presence of the polymer is indicative of a target nucleic acid molecule being present. In an embodiment, the sequence of the target nucleic acid molecule can be determined from the monomers and dimers that were used as the building blocks for the polymer. In embodiments, monomers form dimers in the presence of a target nucleic acid molecule, and the one or both of the monomers in each dimer can comprise functional moieties to aid in determining which monomers were used to form the polymer. In an embodiment, the functional moieties can be selected from the group consisting of DNA capture probes, fluorescent dyes, quantum dots (QDs), and gold nanoparticles (AuNPs).

In embodiments, the monomers are formed from an X-shaped nucleic acid. In an embodiment, the monomers are formed from an X-shaped nucleic acid and one or more Y-shaped nucleic acids. In another embodiment, the monomers are formed from an X-shaped nucleic acid and two or more Y-shaped nucleic acids. In yet another embodiment, the monomers are formed from an X-shaped nucleic acid and three or more Y-shaped nucleic acids. Methods for forming X-shaped nucleic acids and Y-shaped nucleic acids can be found in the Luo publications.

In embodiments of the invention, methods for detecting the presence of a target nucleic acid molecule comprise providing a first ABC monomer (also "monomer" herein) and a second ABC monomer to a solution comprising the target nucleic acid. Each of the first monomer (monomer 1) and second monomer (monomer 2) can be formed from an X-shaped nucleic acid and one or more Y-shaped nucleic acids. In an embodiment, the first monomer links to the second monomer with the aid of the target nucleic acid molecule to form a dimer (also "monomer (1+2)" herein). Next, the dimer is polymerized to form a polymer.

In an embodiment of the invention, an ABC monomer can comprise branched nucleic acids. The monomer can comprise one or more different moieties, and the one or more different moieties can be conjugated to the nucleic acid. The nucleic acid can be DNA or RNA, such as Y-DNA or X-DNA.

In an embodiment, a monomer can be formed using a branched, different moiety-conjugated Y-shaped nucleic acid as a modular donor ("donor") and an X-shaped nucleic acid as a core acceptor molecule ("acceptor"). Anisotropy can be achieved by designing unique nucleic acid sequences at the end of each branch of the core X-shaped nucleic acid. Without being bound by theory, the freedom in synthesizing any desired DNA sequence at any position can permit increased capacity of anisotropy from different sequences.

With reference to FIG. 1, in an embodiment of the invention, the assembly of ABC monomer 1 and ABC monomer 2 to form an ABC monomer (1+2) (also "ABC dimer" herein) and subsequent polymerization to form a nano-architecture (also "ABC polymer" herein) is illustrated. In the illustrated embodiment, monomers 1 and 2 are each formed from an X-DNA, three Y-DNAs and single-stranded bridge DNAs. Each of the Y-DNAs comprises a functional moiety (illustrated by triangles, boxes, circles, ovals, pentagons and stars). While the Y-DNAs comprise functional moieties, in some embodiments, only a subset of the Y-DNAs can have functional moieties. For example, only the Y-DNAs used to form monomer 1 (or 2) can include functional moieties, and the Y-DNAs used to form monomer 2 (or 1) can be devoid of functional moieties.

Multi-functionality of a nano-structure as provided herein can be obtained using specific connection of different donor Y-shaped nucleic acid to the same acceptor X-shaped nucleic acid. For example, single-stranded bridge DNA, whose sequence is complementary to both acceptor and donor sequences, can be used to connect Y-shaped nucleic acids with an X-shaped nucleic acid. In the illustrated embodiment, each unique end-sequence is designated West, North, and East—W, N, and E for Y-DNA, and W', N', and E' for X-DNA according to the branch orientation (see FIG. 1). The bridge DNAs are similarly designated by w, n, and e.

With continued reference to FIG. 1, a Y-DNA of monomer 1 can include a linker (having a linker or linking sequence) that is at least partially complementary to a linker of a Y-DNA of monomer 2. In the illustrated embodiment, the linker of monomer 1 (linker 1) is at least partially complementary to the linker of monomer 2 (linker 2). In an embodiment, linkers 1 and 2 are entirely complementary to one another. Linkers 1 and 2 aid in the formation of the dimer (ABC monomer (1+2), as illustrated).

With continued reference to FIG. 1, in a preferable embodiment, monomer 1 and monomer 2 can be provided to a solution (or sample) comprising a complementary linker (having a linker or linking sequence) ("Complementary linker (1+2)", as illustrated). In an embodiment, the complementary linker has a sequence that is partially complementary to linker 1 and partially complementary to linker 2. The complementary linker aids in the formation of the dimer, the dimer comprising monomer 1 and monomer 2. In an embodiment, the complementary linker is a target nucleic acid, such as the target nucleic acid of a pathogen.

In an embodiment, a dimer will form only if a target nucleic acid that is complementary to linker 1 and linker 2 is present. That is, the dimer will form only if the target nucleic acid is a complementary linker. In such a case, a user may provide monomer 1 and monomer 2 to a solution comprising a nucleic acid. If the nucleic acid is complementary to linker 1 and linker 2, a dimer will form. The dimer can then be subjected to a stimulus (e.g., UV light) to induce polymerization, thus forming a polymer.

In an embodiment, the stimulus is light. For example, a Y-shaped nucleic acid of each of monomer 1 and monomer 2 includes a photo-crosslinkable moiety. Methods of linking nucleic acid structures via photocrosslinking are presented in PCT Patent Application PCT/US2009/52795, filed Aug. 5, 2009 and entitled "PHOTO-CROSSLINKING-BASED METHOD FOR CREATING DNA HYDROGELS," which application is incorporated by reference herein in its entirety. When dimers are formed having Y-shaped nucleic acids including photo-crosslinkable moieties, polymerization can be induced by exposing the sample or solution comprising the dimers to a stimulus, such as light (e.g., UV light).

In some embodiments, the stimulus comprises an enzyme, e.g., a ligase. Ligation refers to the process of joining DNA molecules together with covalent bonds. For example, DNA ligation involves creating a phosphodiester bond between the 3' hydroxyl of one nucleotide and the 5' phosphate of another. Ligation can be carried out in presence of a ligase enzyme under suitable reaction conditions, e.g., at 4-37° C. Suitable ligases include *Thermus thermophilus* ligase, *Thermus acquaticus* ligase, *E. coli* ligase, T4 ligase, and *Pyrococcus* ligase. Methods of linking branched DNA through enzyme ligation are found in, e.g., U.S. patent application Ser. Nos. 11/464,184, filed Aug. 11, 2006 and entitled "NUCLEIC ACID-BASED MATRIXES FOR PROTEIN PRODUCTION;" 11/464,181, filed Aug. 11, 2006 and entitled "NUCLEIC ACID-BASED MATRIXES."

In some embodiments, the methods of the invention further comprise quantifying the amount of target nucleic acid present in the sample. For example, FIG. 13 illustrates an increase in detected signal corresponding to the amount of target present, in this case pathogenic DNA. Thus, the methods can be used to quantify the amount of starting target nucleic acid in solution.

In an aspect, the invention provides a composition comprising an X-shaped nucleic acid hybridized to one or more Y-shaped nucleic acids, wherein the composition comprises a sequence that is complementary to a target nucleic acid. The target nucleic acid can be a sequence that is desirable to be detected, e.g., a sequence indicative of a condition such as a disease state or environmental contaminant. The complementary sequence of the composition can be chosen to avoid undesired binding events, such as hybridization to other X- and Y-shaped nucleic acids of the invention, or other background (e.g., non-target) nucleic acid sequences that may be present in the sample. The disease state can comprise the presence of a pathogenic microorganism. In some embodiments, the complementary sequence of the composition can be chosen to hybridize to a target sequence indicative of a number of pathogens, e.g., recognizing a conserved sequence amongst a family of bacteria. In some embodiments, the complementary sequence of the composition can be chosen to hybridize to a target sequence indicative of a number of pathogens, e.g., recognizing a single species of bacteria. The target can also be host nucleic acids, such as altered chromosomal DNA or differentially expressed mRNAs indicative of a condition, e.g., cancer or infection. One of skill will appreciate that the nucleic acids of the invention can be designed to hybridize with any appropriate nucleic acid target and thus can be used to detect the presence or absence of nucleic acids in a wide variety of settings.

In embodiments of the invention, a composition, e.g., a reagent, for detecting the presence of a target nucleic acid comprises a first monomer having a first X-shaped nucleic acid, a first Y-shaped nucleic acid and a second Y-shaped nucleic acid. The first Y-shaped nucleic acid can have a linker sequence that is complementary to a portion of a sequence of the target nucleic acid, and the second Y-shaped nucleic acid can include a crosslinkable moiety. The composition can further comprise a second monomer having a second X-shaped nucleic acid, a third Y-shaped nucleic acid and a fourth Y-shaped nucleic acid. The third Y-shaped nucleic acid can include a linker sequence that is complementary to a portion of the sequence of the target nucleic acid, and the fourth Y-shaped nucleic acid can include a crosslinkable moiety.

In an embodiment, the crosslinkable moiety is a carbon-to-carbon double bond or other photoreactive moiety that is sensitive to electromagnetic radiation as described herein. In some embodiments, the photoreactive group comprises a vinyl, acrylate, N-hydroxysuccinimide, amine, carboxylate or thiol moiety. In some embodiments, the photoreactive group is a primary amine modified group, a secondary amine modified group, or a tertiary amine modified group. The photocrosslinking step can be performed under electromagnetic radiation, e.g., in the visible, ultraviolet (UV), near infrared, infrared, and/or microwave regions. Photo-reactive amino acid analogs include photoreactive diazirine analogs to leucine and methionine. L-Photo-Leucine and L-Photo-Methionine are analogs of the naturally occurring L-Leucine and L-Methionine amino acids and can form crosslinks when exposed to UV light. The photocrosslinking can also be performed using gamma rays, X-rays, or radio waves as appropriate. The photocrosslinking can also be performed using a crosslinker, e.g., a UV crosslinker.

Figure 2A:
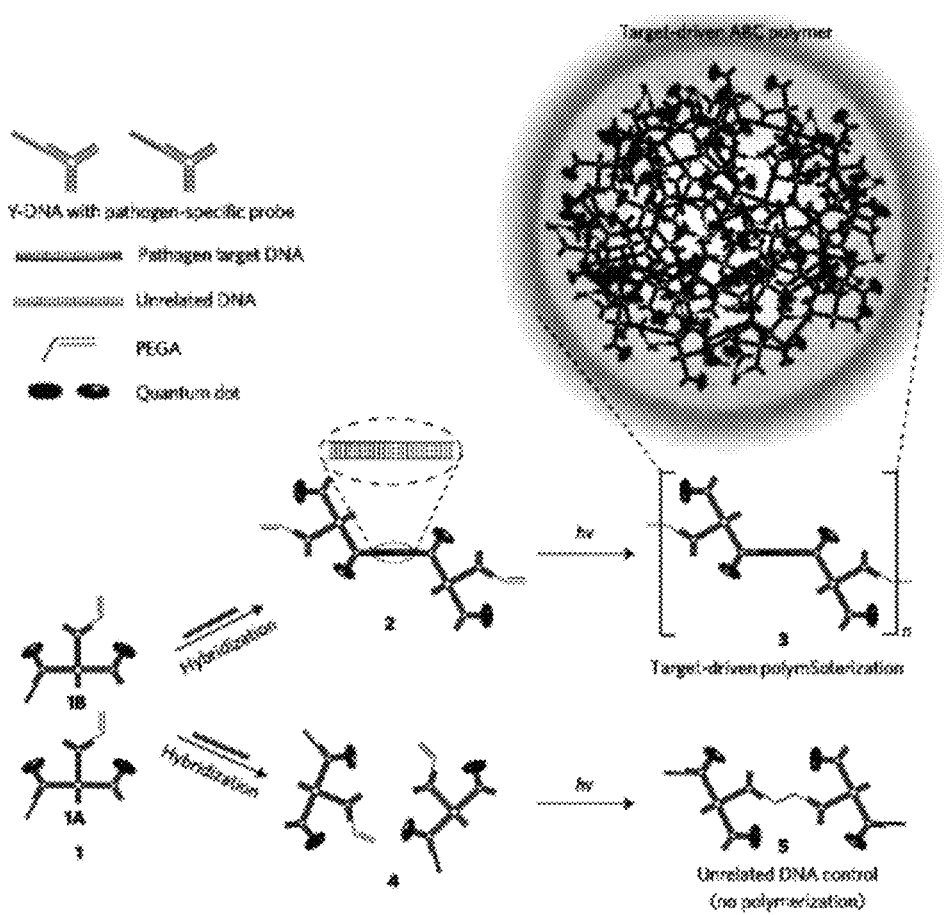
FIG. 2A illustrates a schematic of target-driven polymerization.

With reference to FIG. 2A, a schematic of target-driven polymerization is shown, in accordance with an embodiment of the invention. In a first step, monomers 1A and 1B are provided comprising Y-shaped nucleic acids with pathogen-specific probes. Next, the monomers 1A and 1B are exposed to a pathogen target DNA that is complementary to the pathogen-specific probes of the monomers 1A and 1B. The monomers 1A and 1B react with the pathogen target DNA to form a dimer 2 having the monomers 1A and 1B and the pathogen target DNA. Next, a sample (or solution) having the dimers is exposed to light (hv), which induces (or facilitates) the polymerization of the dimers to form a polymer 3 ("target-driven ABC polymer," as illustrated).

With continued reference to FIG. 2A, in the absence of a target DNA, monomers do not hybridize to form dimers 4. Upon exposure to light, polymerization does not occur, though some crosslinking can occur to form species 5.

In some embodiments, the target nucleic acids comprise pathogen sequences. Pathogens that can be detected using the compositions and methods of the invention include any number of microorganisms, e.g., bacteria, viruses, protozoa, yeast, fungi, and parasites. One of skill will appreciate that the compositions of the invention can be designed to hybridize to, and thereby detect, organisms with known DNA sequences. Exemplary pathogens that can be detected include the SARS coronavirus, *Bacillus anthracis* and Ebola virus. Other pathogens that can be detected include without limitation *Staphylococcus epidermidis*, *Escherichia coli*, methicillin-resistant *Staphylococcus aureus* (MSRA), *Staphylococcus aureus*, *Staphylococcus hominis*, *Enterococcus faecalis*, *Pseudomonas aeruginosa*, *Staphylococcus capitis*, *Staphylococcus wameri*, *Klebsiella pneumoniae*, *Haemophilus influnzae*, *Staphylococcus simulans*, *Streptococcus pneumoniae* and *Candida albicans*. Diseases and causes that can be detected include gonorrhea (*Neisseria gorrhoeae*), syphilis (*Treponena pallidum*), clamydia (*Clamyda tracomitis*), nongonococcal urethritis (*Ureaplasm urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV. Other infectious agents that can be detected include *Pseudomonas aeruginosa*, methicillin-resistant *Staphlocococcus aureus* (MSRA), *Klebsiella pneumoniae*, *Haemophilis influenzae*, *Staphlococcus aureus*, *Stenotrophomonas maltophilia*, *Haemophilis parainfluenzae*, *Escherichia coli*, *Enterococcus faecalis*, *Serratia marcescens*, *Haemophilus parahaemolyticus*, *Enterococcus cloacae*, *Candida albicans*, *Moraxiella catarrhalis*, *Streptococcus pneumoniae*, *Citrobacter freundii*, *Enterococcus faecium*, *Klebsella oxytoca*, *Pseudomonas fluorscens*, *Neiseria meningitidis*, *Streptococcus pyogenes*, *Pneumocystis carinii*, *Klebsella pneumoniae Legionella pneumophila*, *Mycoplasma pneumoniae*, and *Mycobacterium tuberculosis*.

Viruses that can be detected include without limitation family members of Astroviridae, Caliciviridae, Picornaviridae, Togaviridae, Flaviviridae, Caronaviridae, Paramyxviridae, Orthomyxoviridae, Bunyaviridae, Arenaviridae, Rhabdoviridae, Filoviridae, Reoviridae, Bornaviridae, Retroviridae, Poxyiridae, Herpesviridae, Adenoviridae, Papovaviridae, Parvoviridae, Hepadnaviridae, Coxsackie A-24 virus Adenovirus 11, Adenovirus 21, Coxsackie B virus, Borna Diease Virus, Respiratory syncytial virus, Parainfluenza virus, California encephalitis virus, human papilloma virus, varicella zoster virus, Colorado tick fever virus, Herpes Simplex Virus, vaccinia virus, parainfluenza virus 1, parainfluenza virus 2, parainfluenza virus 3, dengue virus, Ebola virus, Parvovirus B19 Coxsackie A-16 virus, HSV-1, hepatitis A virus, hepatitis B virus, hepatitis C virus, hepatitis D virus, hepatitis E virus, human immunodeficiency virus, Coxsackie B1-B5, Influenza viruses A, B or C, LaCross virus, Lassavirus, rubeola virus Coxsackie A or B virus, Echovirus, lymphocytic choriomeningitis virus, HSV-2, mumps virus, Respiratory Synytial Virus, Epstein-Barr Virus, Poliovirus Enterovirus, rabies virus, rubivirus, variola virus, WEE virus, Yellow fever virus or varicella zoster virus.

Bacteria that can be detected include without limitation members of the *S. pyrogenes*, *S. agalactiae*, *S. equi*, *S. canis*, *S. bovis*, *S. equinus*, *S. anginosus*, *S. sanguis*, *S. salivarius*, *S. mitis*, *S. mutans*, *S pyogenes*, *Enterococcus faecalis*, *Enterococcus faecium*, *Staphylococcus epidermidis*, *Staphylococcus aureus*, *Hemophilus influenzae*, *Pseudomonas aeruginosa*, *Pseudomonas pseudomallei*, *Pseudomonas mallei*, *Brucella melitensis*, *Brucella suis*, *Brucella abortus*, *Bordetella pertussis*, *Neisseria meningitidis*, *Neisseria gonorrhoeae*, *Moraxella catarrhalis*, *Corynebacterium diphtheriae*, *Corynebacterium ulcerans*, *Corynebacterium pseudotuberculosis*, *Corynebacterium pseudodiphtheriticum*, *Corynebacterium urealyticum*, *Corynebacterium hemolyticum*, *Corynebacterium equi*, *Listeria monocytogenes*, *Nocardia asteroides*, *Bacteroides* species, *Actinomycetes* species, *Treponema pallidum*, *Leptospirosa* species, *Klebsiella pneumoniae*; *Escherichia coli*, *Proteus*, *Serratia* species, *Acinetobacter*, *Yersinia pestis*, *Francisella tularensis*, *Enterobacter* species, *Bacteriodes* species or *Legionella* species.

Fungi that can be detected include without limitation members of the *Aspergillus* sp., *Dermatophytes*, *Blastomyces derinatatilis*, *Candida* sp., *Malassezia furfur*, *Exophiala werneckii*, *Piedraia hortai*, *Trichosporon beigelii*, *Pseudallescheria boydii*, *Madurella grisea*, *Histoplasma capsulatum*, *Sporothrix schenckii*, *Histoplasma capsulatum T. rubrum*, *T. interdigitale*, *T. tonsurans*, *M. audouini*, *T. violaceum*, *M. ferrugineum*, *T. schoenleinii*, *T. megninii*, *T. soudanense*, *T. yaoundei*, *M. canis*, *T. equinum*, *T. erinacei*, *T. verrucosum*, *M. nanum* (originating from pigs), *M. distortum*, *M. gypseum* or *M. fulvum* families.

Protozoa that can be detected include without limitation members of the *Cryptosporidium*, *Isospora belli*, *Toxoplasma gondii*, *Trichomonas vaginalis*, *Cyclospora* species.

Various plant pathogens can also be detected, including without limitation *Alternaria* spp.; *Armillaria mellae*; *Arthrobotrys oligosporus*; *Boletus granulatus*; *Botrytis fabae*; *Botritis cinerea*; *Candida albicans*; *Claviceps purpurea*; *Cronartium ribicola*; *Epicoccum purpurescens*; *Epidermophyton floccosum*; *Fomes annosus*; *Fusarium oxysporum*; *Gaeumannomyces graminis* var. *tritici*; *Glomerella cingulata*; *Gymnosporangium juniperi-virginianae*; *Microsporum canis*; *Monilinia fructicola*; *Physoderma alfalfae*; *Phytopthera infestans*; *Pityrosporum orbiculare* (*Malassezia furfur*); *Polyporus sulphureus*; *Puccinia* spp.; *Saccharomyces cerevisiae*; *Septoria apiicola*; *Trichophyton rubrum*; *T. mentagrophytes*; *Ustilago* spp.; *Venturia inaequalis*; or *Verticillium dahliae*.

Other non-limiting examples of microorganisms and pathogens that can be detected by the compositions and methods of the invention include without limitation those listed in U.S. Patent Publication No. 2004/0197845, filed on Jul. 24, 2003 and entitled "Methods and Apparatus for Pathogen Detection, Identification and/or Quantification," which application is incorporated by reference herein in its entirety. For example, such targets include *Actinobacillus* spp., *Actinomyces* spp., Adenovirus (types 1, 2, 3, 4, 5 et 7), Adenovirus (types 40 and 41), *Aerococcus* spp., *Aeromonas hydrophila, Ancylostoma duodenale, Angiostrongylus cantonensis, Ascaris lumbricoides, Ascaris* spp., *Aspergillus* spp., *Bacillus anthracis, Bacillus cereus, Bacteroides* spp., *Balantidium coli, Bartonella bacilliformis, Blastomyces dermatitidis, Bluetongue virus, Bordetella bronchiseptica, Bordetella pertussis, Borrelia burgdorferi, Branhamella catarrhalis, Brucella* spp., *B. abortus, B. canis, B. melitensis, B. suis, Brugia* spp., *Burkholderia mallei, Burkholderia pseudomallei, Campylobacter fetus* subsp. *Fetus, Campylobacter jejuni, C. coli, C. fetus* subsp. *Jejuni, Candida albicans, Capnocytophaga* spp., *Chlamydia psittaci, Chlamydia trachomatis, Citrobacter* spp., *Clonorchis sinensis, Clostridium botulinum, Clostridium difficile, Clostridium perfringens, Clostridium tetani, Clostridium* spp., *Coccidicides immitis*, Colorado tick fever virus, *Corynebacterium diphtheriae, Coxiella burnetii*, Coxsackievirus, Creutzfeldt-Jakob agent, Kuru agent, Crimean-Congo hemorrhagic fever virus, *Cryptococcus neoformans, Cryptosporidium parvum*, Cytomegalovirus Dengue virus (1, 2, 3, 4), Diphtheroids Eastern (Western) equine encephalitis virus, Ebola virus, *Echinococcus granulosus, Echinococcus multilocularis, Echovirus, Edwardsiella tarda, Entamoeba histolytica, Enterobacter* spp., Enterovirus 70, *Epidermophyton floccosum, Microsporum* spp., *Trichophyton* spp., Epstein-Barr virus, enterohemorrhagic *Escherichia coli*, enteroinvasive *Escherichia coli*, enteropathogenic *Escherichia coli*, enterotoxigenic *Escherichia coli, Fasciola hepatica, Francisella tularensis, Fusobacterium* spp., *Gemella haemolysans, Giardia lamblia, Giardia* spp., *Haemophilus ducreyi, Haemophilus influenzae* (group b), Hantavirus, Hepatitis A virus, Hepatitis B virus, Hepatitis C virus, Hepatitis D virus, Hepatitis E virus, Herpes simplex virus, *Herpesvirus simiae, Histoplasma capsulatum, Human coronavirus*, Human immunodeficiency virus, Human papillomavirus, Human rotavirus, Human T-lymphotrophic virus, Influenza virus, Junin virus/Machupo virus, *Kiebsiella* spp., Kyasanur Forest disease virus, *Lactobacillus* spp., *Legionella pneumophila, Leishmania* spp., *Leptospira interrogans, Listeria monocytogenes*, Lymphocytic choriomeningitis virus, Marburg virus, Measles virus, *Micrococcus* spp., *Moraxella* spp., *Mycobacterium* spp., *Mycobacterium tuberculosis, M. bovis, Mycoplasma hominis, M. orale, M. salivarium, M. fermentans, Mycoplasma pneumoniae, Naegleria fowleri, Necator americanus, Neisseria gonorrhoeae, Neisseria meningitidis, Neisseria* spp., *Nocardia* spp., Norwalk virus, Omsk hemorrhagic fever virus, *Onchocerca volvulus, Opisthorchis* spp., Parvovirus B19, *Pasteurella* spp., *Peptococcus* spp., *Peptostreptococcus* spp., *Plesiomonas shigelloides*, Powassan encephalitis virus, *Proteus* spp., *Pseudomonas* spp., Rabies virus, Respiratoiy syncytial virus, Rhinovirus, *Rickettsia akari, Rickettsia prowazekii, R. canada, Rickettsia rickettsii*, Ross river virus/O'Nyong-Nyong virus, Rubella virus, *Salmonella choleraesuis, Salmonella paratyphi, Salmonella typhi, Salmonella* spp., *Schistosoma* spp., Scrapie agent, *Serratia* spp., *Shigella* spp., Sindbis virus, *Sporothrix schenckii*, St. Louis encephalitis virus, Murray Valley encephalitis virus, *Staphylococcus aureus, Streptobacillus moniliformis, Streptococcus agalactiae, Streptococcus faecalis, Streptococcus pneumoniae, Streptococcus pyogenes, Streptococcus salivarius, Taenia saginata, Taenia solium, Toxocara canis, T. cati, Toxoplasma gondii, Treponema pallidum, Trichinella* spp., *Trichomonas vaginalis, Trichuris trichiura, Trypanosoma brucei, Ureaplasma urealyticum*, Vaccinia virus, Varicella-zoster virus, Venezuelan equine encephalitis, Vesicular stomatitis virus, *Vibrio cholerae*, serovar 01, *Vibrio parahaemolyticus, Wuchereria bancrofti*, Yellow fever virus, *Yersinia enterocolitica, Yersinia pseudotuberculosis*, and *Yersinia pestis*.

In addition to pathogens, the compositions of the invention can be used to detect host abnormalities, e.g., the presence or absence of a certain transcript or chromosomal aberration, such as a mutation, deletion, insertion or break. Such detection can be used to diagnose a human disease, e.g., a cancer.

Delivery Vectors

In another aspect of the invention, biological nano-structures can be used for delivery, e.g., of drugs and other biologically active agents. In embodiments, the ABC monomers disclosed herein can be used for drug delivery, such as multi-drug delivery. Polymerized spheres can be delivered to cells with both biologically active agents and tracers, e.g., oligodeoxynucleotides and QDs. Internalization by cells can be determined using microscopy images. In some embodiments, the cell internalization is without use of a transfection reagent. Furthermore, the ABC polymers can provide minimal or low cytotoxicity.

In embodiments, a composition for delivery comprises a first dimer having a first monomer and a second monomer. Each of the first and second monomers comprises an X-shaped nucleic acid that is linked to one or more Y-shaped nucleic acids. The first monomer comprises a Y-shaped nucleic acid that is linked to a Y-shaped nucleic acid of the second monomer via a complementary linker. In a preferable embodiment, the complementary linker of the composition is configured to be recognized by a target cell. In some embodiments, the recognition comprises transcription of the linker by the cell. In such a case, the complementary linker can be referred to as a "transcribeable linker". As an example, the complementary linker can be transcribed by the target cell following endocytosis of the composition by the target cell. In some embodiments the recognition comprises recognized by a specific cell, binding to the surface of a cell (with or without endocytosis); interaction with a specific cell; harming a cell; or moving into spatial proximity to a particular cell. In an embodiment, the complementary linker is an oligonucleotide. Other linkers including chemicals capable of conjugation can also be used.

In an embodiment, the delivery composition further comprises a second dimer having a third monomer and a fourth monomer. Each of the third and fourth monomers comprises an X-shaped nucleic acid that is linked to one or more Y-shaped nucleic acids. In an embodiment, the third monomer comprises a Y-shaped nucleic acid that is linked to a Y-shaped nucleic acid of the fourth monomer. In an embodiment, the third and fourth monomers are linked with the aid of a complementary linker. The third monomer comprises one or more Y-shaped nucleic acids hybridized to a nucleic acid molecule that is configured to be recognized by a target cell. In an embodiment, the nucleic acid molecule is a small interfering (or short interfering) ribonucleic acid (RNA) molecule, known as siRNAs, micro RNAs (miRNA), antisense oligonucleotides, a gene sequences, a regulatory DNA sequence, a regulatory RNA sequence, a peptide nucleic acid (PNA), locked nucleic acid (LNA), inaccessible RNA, and the like.

In an embodiment, a Y-shaped nucleic acid of the first dimer is crosslinked to the Y-shaped nucleic acid of the second dimer. This can be accomplished by providing dimers having crosslinkable (e.g., photocrosslinkable) moieties, such as polyethylene glycol monoacrylate (PEGA). Crosslinking can then be induced by a stimulus, such as light (e.g., UV light). The crosslinking can also be performed enzymatically, e.g., using a ligase, or through chemical crosslinking moieties as described herein.

In an embodiment, the first, second, third and/or fourth monomers comprise two Y-shaped nucleic acids linked to one X-shaped nucleic acid. In another embodiment, the first, second, third and/or fourth monomers comprise three Y-shaped nucleic acids linked to one X-shaped nucleic acid. In yet another embodiment, the first, second, third and/or fourth monomers comprise four Y-shaped nucleic acids linked to one X-shaped nucleic acid. Additionally, one or more Y-shaped nucleic acids of one or more of the first, second, third and fourth monomers can comprise a functional moiety, such as a fluorescence dye or quantum dot (see above).

In an embodiment, the complementary linker of the composition has a sequence that is partially complementary to a linker sequence of a Y-shaped nucleic acid of each of the first and second monomers. In an embodiment, the third and fourth monomers are linked by a linking sequence that is partially complementary to a Y-shaped nucleic acid of each of the third and fourth monomers. In an embodiment, the linking sequence can be configured to be transcribed by a target cell.

In an embodiment, a Y-shaped nucleic acid of the first monomer can be linked to an X-shaped nucleic acid of the first monomer via a bridge DNA having a sequence that is complementary to a donor sequence of the Y-shaped nucleic acid and an acceptor sequence of the X-shaped nucleic acid.

The delivery composition can have various shapes and configurations. In an embodiment, the composition comprises a polymerized sphere.

In an embodiment, a composition formed using the first, second, third and fourth monomers can have a single type of complementary linker for a single type of biologically active agent. In another embodiment, the composition comprises a plurality of complementary linkers for a plurality of biologically active agents. This advantageously provides for simultaneously delivering a plurality of biologically active agents to a subject.

In an embodiment, the composition, formed using one or more types of complementary linkers, is delivered to a subject. A "subject," "individual" or "patient" is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The delivery composition of the invention can enter the subject's cells, e.g., via endocytosis, or remain bound to the surface of the cell. In an embodiment, the subject's cells transcribe one or more of the one or more types of complementary linkers to produce proteins or change metabolic events that facilitate the patient's healing process. In an embodiment, the complementary linkers code for one or more biologically active agents that facilitate the destruction of malignant cells. In addition, the nucleic acids of the invention can be linked to other biologically active agents.

It will be appreciated that the compositions of the invention can be implanted in a subject using methods known in the art, including invasive, surgical, minimally invasive and non-surgical procedures. The compositions described herein are suitable for use in various locations in the body. For example, they can be implanted on the surface of the skin, under the skin, or in or near internal tissues or organs. The compositions in some embodiments are located in or near a gastro-intestinal tract, airway tissue or organ, cardiovascular tissue or organ, or neuronal tissue or organ. Other examples of target sites for implantation include but are not limited to the eye, pancreas, kidney, liver, stomach, muscle, heart, lungs, lymphatic system, thyroid gland, pituitary gland, ovaries, prostate, skin, endocrine glands, ear, breast, urinary tract, brain or any other site in an animal.

In certain embodiments, the compositions of the invention can be encased in a nonbiodegradable material, which materials are known in the art. For example, a composition of the invention is attached to a temporary implant, the composition can be encased in a nonbiodegradable casing. Suitable materials for casings include but are not limited to poly(dimethylsiloxane), silicone elastomers, polyurethane, poly(tetrafluoroethylene), polyethylene, polysulfone, poly(methyl methacrylate), poly(2-hydroxyethyl methacrylate), polyacrylonitrile, polyamides, polypropylene, poly(vinyl chloride), poly(ethylene-co-(vinyl acetate)), polystyrene, poly (vinyl pyrrolidine), yellow wax, petrolatum cholesterol, stearyl alcohol, white wax, white petrolatum, methylparaben, propylparaben, sodium lauryl sulfate, propylene glycol, glycerogelatins, gelling agents such as carbomer 934, cellulose derivatives, natural gums, penetration enhancers such as dimethyl sulfoxide, ethanol propylen glycol, glycerin, urea, glycerogelatins, coloring agents, lactose, stearic acid, starch glycolate, sugar, gelatin, fixed vegetable oils and fats, glycerin, propylene glycol, alcohol, ethyl oleate, isopropyl myristate, dimethyl acetamide, and mixtures or aqueous or oil based dispersions of these.

Selection of implantation sites for the composition are within the skill of one of skill in the art. For example, suitable sites for implantation in the eye include the anterior chamber, posterior chamber, vitreous cavity, suprachoroidal space, subconjunctiva, episcleral, intracorneal, epicorneal and sclera. Suitable sites extrinsic to the vitreous comprise the suprachoroidal space, the pars plana and the like. The suprachoroid is a potential space lying between the inner scleral wall and the apposing choroid. Matrixes implanted in a suprachoroid may deliver drugs to the choroid and to the anatomically apposed retina, depending upon the diffusion of the drug from the implant, the concentration of drug comprised in the implant and the like. Additional methods and procedures for implanting a device of the invention in various tissue/organ sites are known in the art, such as disclosed in U.S. Pat. Nos. 7,013,177; 7,008,667; 7,006,870; 6,965,798; 6,963,771; 6,585,763; 6,572,605; or 6,419,709, the disclosure of each of which is herein incorporated by reference.

In another embodiment the matrix provides a means for topical delivery, such as to skin. For example, the composition can be encased in a nondegradable casing (e.g., plastics or bandage or patch) providing an aperture or surface for contacting the target site (i.e., skin). Subsequently, the composition can be released, e.g., in a time controlled manner, to the target site.

Any number of biologically active agents can be linked to the compositions of the invention to provide multi-functionality. Examples of drug agents for use with the invention are described in PCT Patent Application PCT/US2009/52795, filed Aug. 5, 2009 and entitled "PHOTO-CROSSLINKING-BASED METHOD FOR CREATING DNA HYDROGELS," which application is incorporated by reference herein in its entirety.

Multifunctional Polymers

Figure 4:
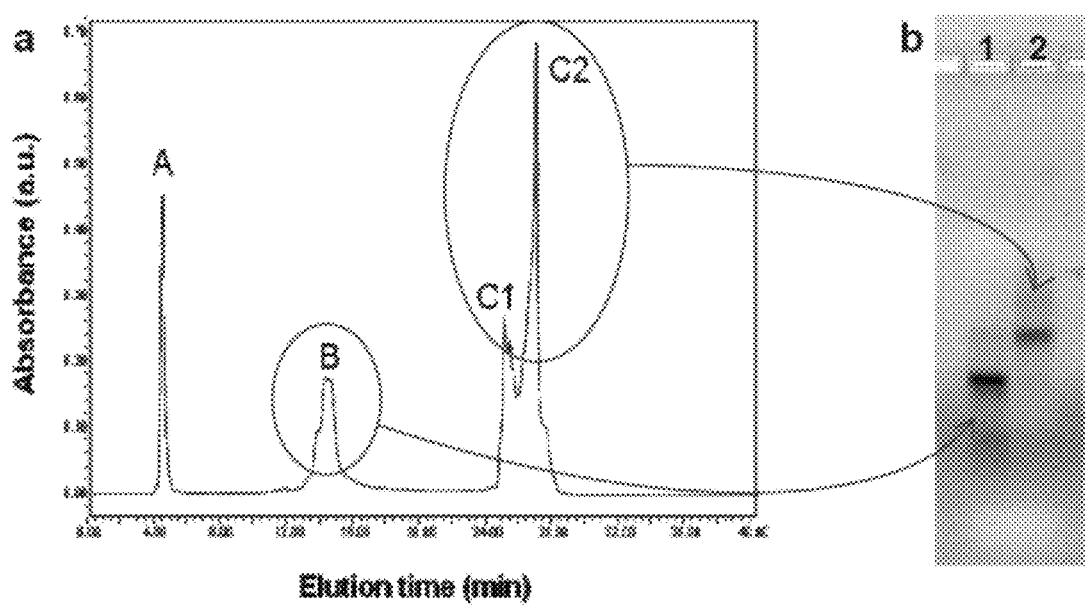
FIG. 4A illustrates an HPLC chromatogram of PEGA and Y-DNA conjugation reaction, in accordance with an embodiment of the invention. The separation of PEGA-NHS (A), NH2-Y-DNA (B), and PEGA-Y-DNA (C1, C2) were achieved by a gradient elution.
FIG. 4B illustrates gel electrophoresis (3% agarose gel, EtBr staining) of HPLC fractions, in accordance with an embodiment of the invention.
Figure 5:
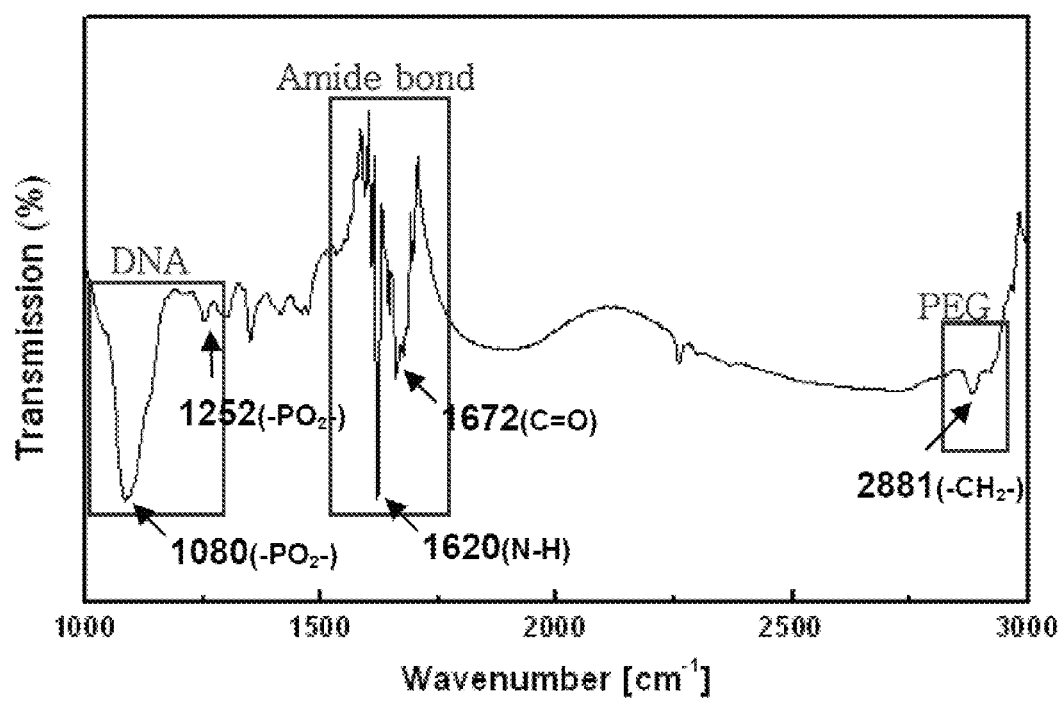
FIG. 5 illustrates Fourier transform infrared (FTIR) spectra (KBr) of PEGA-Y-DNA in the region of 3000 to 1000 cm-1. Transmittance bands at 1080 and 1252 cm-1 in both spectra belong to PO2 of DNA; 1620 cm-1 belongs to N—H of amide bond (amide II) and 1672 cm-1 belongs to C=O of amide bond (amide I). 2881 cm-1 belongs to CH2 of PEG, in accordance with an embodiment of the invention.

In an aspect of the invention, due to built-in modularity, many types of moieties can be linked to a Y-shaped nucleic acid. To build up a multifunctional polymer from ABC monomers, different modules can be designed separately, including DNA capture probes, fluorescent dyes, quantum dots (QDs), and gold nanoparticles (AuNPs) (for DNA sequences, see FIGS. 19 and 20). In addition, by incorporating a photoreactive moiety into a Y-shaped nucleic acid, photo-crosslinkability can be integrated (see, for example, FIGS. 3-5). The resulting ABC monomers, with five different functional groups, can be further photopolymerized using the built-in photo reactive groups. Furthermore, the ABC monomers disclosed herein can be used to build nano-structures with increased precision (or accuracy).

In an embodiment, a first monomer can be prepared with Y-shaped nucleic acids having a first set of functional moieties and a second monomer can be prepared with Y-shaped nucleic acids having a second set of functional moieties, each of the first and second set of functional moieties can be selected from one or more of DNA capture probes, fluorescent dyes, quantum dots (QDs), gold nanoparticles (AuNPs), or other moieties as described herein. The monomers can then be used for target-drive polymerization (see FIG. 1) or to form a dimer having a complementary linker, such as a delivery vector for a biologically active agent. Subsequent polymerization of the dimer (via exposure to UV light, for example) can lead to a multifunctional polymer.

In some embodiments, the ABC monomers within one molecule can carry different fluorescence dyes (see FIGS. 6 and 7). With reference to FIG. 6, the different fluorescence dyes can be of a predetermined ratio. With reference to FIG. 6A, a gel electrophoresis image can reveal lines with different colors based on the fluorescence dyes that were used to prepare one or more of the Y-DNAs in the monomers that were subsequently used to form polymers. A Y-DNA having a first fluorescence dye (1) exhibits a first color 610; a Y-DNA having a second fluorescence dye (2) exhibits a second color 620; and a Y-DNA having the second and third fluorescence dyes exhibits a third color 630. In an embodiment, the first, second and third colors are different from one another.

The ABC monomers and/or polymers formed using the monomers can be characterized using gel electrophoresis (see FIGS. 6 and 7). In an embodiment, this can aid in determining whether a target nucleic acid was present in a sample or solution. The fluorescence colors of the ABC monomers can correspond to the combinations of donor Y-DNAs. In some embodiments, bridge DNAs can be used. For example, to link two different configurations of fluorescence dyes simultaneously onto two different branches of a single X-DNA, two bridge DNAs can be added simultaneously (see FIG. 6b, lanes 5, 6, and 7). By adding all three bridge DNAs, all three different donor Y-DNAs can be anisotropically linked onto the X-DNA simultaneously in a controlled fashion (see FIG. 6b, lane 8). This provides a robust and efficient approach for forming ABC monomers. In an embodiment, the yield of ABC DNA monomers is greater than or equal to 50%, or greater than or equal to 55%, or greater than or equal to 60%, or greater than or equal to 65%, or greater than or equal to 70%, or greater than or equal to 75%, or greater than or equal to 80%, or greater than or equal to 85%, or greater than or equal to 90%, or greater than or equal to 95%.

Figure 8:
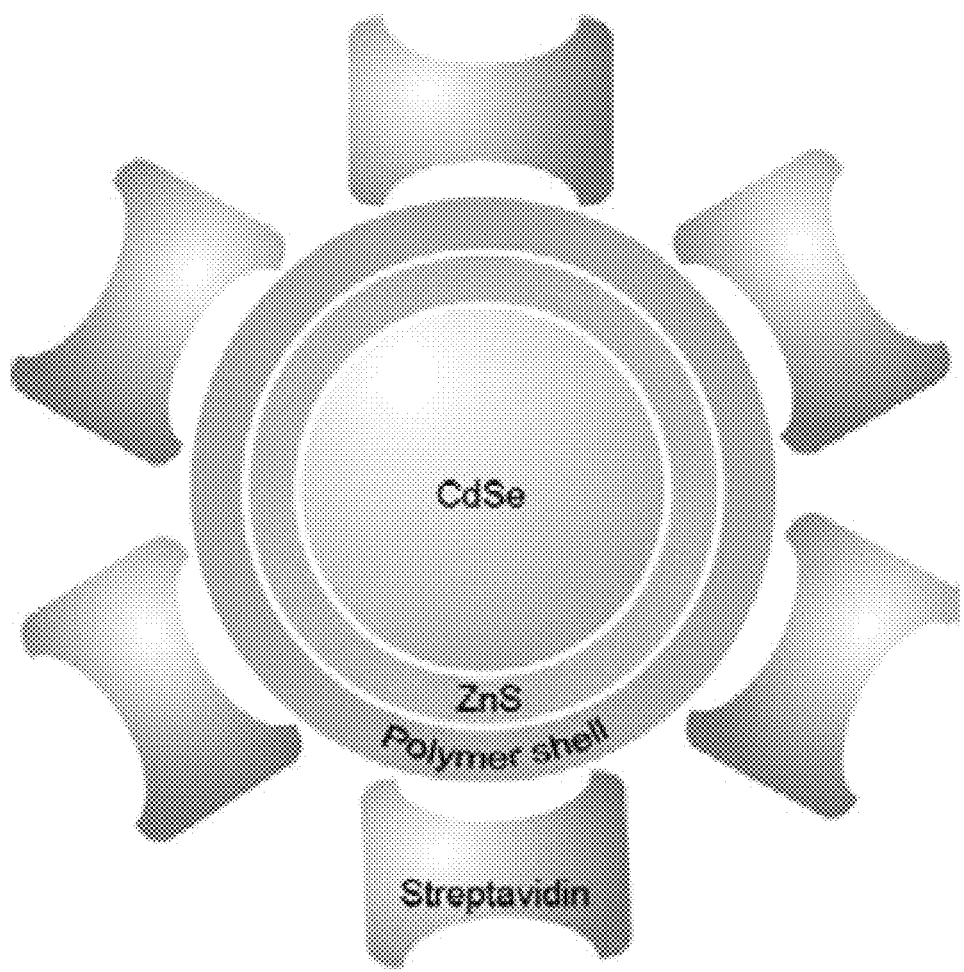
FIG. 8 is a schematic drawing of the structure and composition of a quantum dot (QD), in accordance with an embodiment of the invention.

In an embodiment, the ABC monomers and/or polymers formed using the monomers can be characterized at the individual molecule level. In an embodiment, this can aid in determining whether a target nucleic acid was present in a sample or solution. Donor Y-shaped nucleic acids tethered with two different types of nanoparticles can be generated. For example, the nanoparticle can be a gold (Au) nanoparticle (AuNP) or a quantum dot (QD) (see FIGS. 8 and 9). Both nanoparticles can be individually visible via a scanning transmission electron microscopy (STEM). Au nanoparticles can be visible via a scanning tunneling microscope (STM) and atomic force microscope (AFM). In addition, QDs are visible at both the bulk and solution scales through their intrinsic fluorescence (FIG. 9b and c). An ABC monomer with two different nanoparticles can be detected, such as in FIG. 6c, where the multi-moieties within one ABC monomer can be detected as two 15 nm rod-shaped QDs and one 5 nm round-shaped AuNP (FIG. 10). These different multi-moieties can be individually and anisotropically placed at an accurate position within one ABC monomer.

Other functional moieties that can be linked to the ABC monomers, e.g., via the Y-shaped DNAs comprise a peptide, a polypeptide, a protein, a lipid, a carbohydrate, an aptamer, an antibody, an antigen, a cell growth factor, a DNA binding agent, a detectable label, a selectable marker, biotin, a pharmaceutical agent, a drug, a small molecule, a therapeutic agent, a receptor molecule, a ligand, a nucleic acid molecule or a substrate.

Additional nucleic acid molecule include but are not limited to siRNA, miRNA, snRNA, a oligodeoxynucleotide (ODN), a gene sequence, an intron sequence, an exon sequence, a non-coding sequence, a peptide nucleic acid (PNA), or an mRNA sequence. The additional nucleic acid molecules can further comprise a coding region.

Additional peptides for use with the invention comprise an adenovirus core peptide, a synthetic peptide, an influenza virus HA2 peptide, a simian immunodeficiency virus gp32 peptide, an SV40 T-Ag peptide, a VP22 peptide, a Tat peptide, or a Rev peptide. In some embodiments, the additional peptide comprises a DNA condensing peptide, DNA protection peptide, endosomal targeting peptide, membrane fusion peptide, nuclear localization signaling peptide, or a protein transduction domain peptide.

Detectable labels for use with the invention include a radio-labeled probe, a fluorophore-labeled probe, a quantum dot-labeled probe, a chromophore-labeled probe, an enzyme-labeled probe, an affinity ligand-labeled probe, an electromagnetic spin labeled probe, a heavy atom labeled probe, or a nanoparticle light scattering labeled probe. In some embodiments, the detectable label comprises a chromophore, a fluorescent moiety, an enzyme, an antigen, a heavy metal, a magnetic probe, a dye, a nanocrystal, a phosphorescent group, a radioactive material, a chemiluminescent moiety, a scattering nanoparticle, a fluorescent nanoparticle, a Raman signal generating moiety, or an electrochemical detection moiety. In some embodiments, the detectable label comprises horseradish peroxidase, alkaline phosphatase, β-galactosidase, acetylcholinesterase, streptavidin, avidin, biotin, an aptamer, an antigen, an antibody, an immunoglobulin, an anti-immunoglobulin, umbelliferone, fluorescein, fluorescein isothiocyanate (FITC), rhodamine, tetramethyl rhodamine, TRITC, eosin, green fluorescent protein, erythrosin, coumarin, methyl coumarin, pyrene, malachite green, stilbene, lucifer yellow, Cascade Blue™, Texas Red, PharRed, allophycocyanin (APC), dichlorotriazinylamine fluorescein, dansyl chloride, R-phycoerythrin, phycoerythrin, a fluorescent lanthanide complex, Europium, Terbium, Cy3, Cy5, Cy7, digoxigenin, dinitrophenyl, a molecular beacon, a fluorescent molecular beacon derivative, luminol, a light scattering material, a plasmon resonant material, gold, silver, a quantum dot, $^{14}C$, $^{123}I$, $^{124}I$, $^{125}I$, $^{131}I$, Technetium-99m ($^{Tc}99m$), $^{35}S$, $^{32}P$ or $^{3}H$.

In some embodiments, the moieties comprise a polymer. Non-limiting examples of applicable polymers include poly (ethylene glycol) (PEG), poly(N-isopropylacrylamide), poly (N-alkylacrylamide), poly(N-n-propylacrylamide), poly(N-isopropylmethacrylamide), a peptide, a polypeptide, poly(ethylene oxide)-poly(propylene oxide)-poly(ethylene oxide), poly(DTEC), dextran-polylactide, elastin-like polypeptides, a polyester, polylactide, poly(L-lactic acid), poly(D,L-lactic acid), poly(lactide-co-glycolides), biotinylated poly(ethylene glycol-block-lactic acid), poly(alkylcyanoacrylate), poly(epsilon-caprolactone), polyanhydride, poly(bis(p-carboxyphenoxy) propane-sebacic acid), poly-orthoester, polyphosphoester, polyphosphazene, polystyrene, polyurethane, poly(amino acid), poly(ethylene oxide), poly(ethylene oxide)-polypropylene-poly(ethylene oxide), poly(lactic acid)-g-poly(vinyl alcohol), poly(ethylene oxide)-poly(L-lactic acid), poly(D,L-lactic-co-glycolic acid)-poly(ethylene glycol), poly(L-lactide-ethylene glycol), poly(ethylene glycol)-co-poly(hydroxyl Acid), poly(vinyl alcohol), poly(lactic acid-co-lysine)-poly(aspartic acid), poly(-caprolactone-co-trimethylene carbonate), poly(L-lactic acid-co-glycolic acid-co-L-serine), poly(propylene fumarate), oligo(poly(ethylene glycol) fumarate), poly(propylene furmarate-co-ethylene glycol), poly(ethylene glycol) di[ethylphosphatidyl(ethylene glycol)methacrylate], poly(N-isopropylacrylamide)-poly(ethylene glycol), poly(N-isopropylacrylamide)-gelatin, poly(N-isopropylacrylamide-acrylic acid) or a derivative of any thereof.

In some embodiments, the moieties comprise a natural or synthetic biocompatible material. Non-limiting examples of biocompatible materials include a poly(ethylene glycol) (PEG) hydrogel matrix, a N-isopropylacrylamide (NiPAAm) hydrogel matrix, a chitosan hydrogel matrix or a derivative of any thereof. Natural biocompatible materials include chitosan, methylcellulose, alginate, hyaluronic acid, agarose, fibrin, gelatin, collagen, dextran, or a derivative of any thereof. Synthetic biocompatible material include hydroxyethyl methacrylate, N-(2-hydroxypropyl)methacrylate, N-vinyl-2-pyrrolidone, N-isopropyl acrylamide, vinyl acetate, acrylic acid, methacrylic acid, polyethylene glycol acrylate/methacrylate, polyethylene glycol diacrylate/dimethacrylate, polyvinyl alcohol, propylene fumarate, or a derivative of any thereof.

In some embodiments, at least a portion of the nucleic acids of the subject composition are linked to a substrate, e.g., a nanoparticle or a microparticle. In some embodiments, the substrate comprises one or more of a noble metal, a transition metal, a semi conductor material or a magnetic material. In some embodiments, the substrate comprises one or more of gold, silver, copper, palladium, platinum, cadmium sulfide (CdS), cadmium selenide (CdSe), titanium dioxide ($TiO_2$), zinc oxide (ZnO), carbon black, 4-phosphonooxy-2,2,6,6-tetramethylpiperidyloxy nitr-oxide, titanium dioxide, cobalt, nickel, iron, iron-cobalt, and magnetite ($Fe_3O_4$). In some embodiments, the substrate comprises glass or polydimethylsiloxane (PDMS).

Due to the modularity and flexibility of the compositions of the invention, these and other moieties can be linked to provide modified functionality as desired.

Multifunctional Nano-Architectures

In an aspect of the invention, an ABC monomer can be used to synthesize multifunctional nano-architectures. In an embodiment, an ABC monomer can be designed such that each ABC monomer possesses two QDs with three different color configurations (2G, 1G1R, or 2R, see FIG. 11), one photo-responsive polyethylene glycol monoacrylate (PEGA) moiety, and one single-stranded oligonucleotide probe that is complementary to a specific pathogen DNA, such as SARS coronavirus, ebola virus, or *Bacillus anthracis* (this unique DNA is termed "capture probe", see 1A and 1B in FIG. 2, and FIG. 12). An ABC dimer can then be formed in the presence of a targeted pathogen nucleic acid, such as a pathogen DNA, as the pathogen nucleic acid can serve as a bridge nucleic acid to link the two ABC monomers (such as monomers 1A and 1B of FIG. 2a) together. UV illumination can permit photo-crosslinking with the dimers but not with monomers (see, e.g., species 3 of FIG. 2a). The ABC monomers can be polymerized using a "target-driven" polymerization where polymers (e.g. diblock co-polymer) can be synthesized in the presence of a specific target nucleic acid. In an embodiment, polymerization can be dependent on a pathogen nucleic acid (such as, e.g., a pathogen DNA) and used to generate detectable polymers for pathogen sensing.

In various embodiments, methods are provided for amplifying signals from a single target-binding event. In an embodiment, each target-driven polymer can contain a unique fluorescence code with a specific ratio of green and red, which makes it possible to detect multiple targets simultaneously. For example, three different pathogen DNAs (SARS, Ebola, and Anthrax) can be used as target DNAs (see FIG. 12 for sequences). An "unknown" DNA can be added, and after target-driven photo-polymerization the resultant spheres can possess an expected color ratio (see FIG. 13), which represents a pre-assigned fluorescence code that can be used to identify the unknown DNA. Atomic force microscopy can be used to image the morphology of the pathogen target-driven polymer.

With reference to FIG. 13e, in some embodiments, the concentration of polymeric spheres (i.e., the number of polymeric spheres per unit area from microscopy images) is linearly proportional to the log of concentrations of target DNA. Thus, the presence of a pathogen nucleic acid can be determined by counting the polymeric spheres under a microscope. In embodiments, the detection limits are between about 100 fM and 1 nM. In some embodiments, the detection limit is less than about 10 nM, 1 nM, 100 fM, 10 fM, or less than about 1 fM. The dynamic range of detection can be about 1, 2, 3, 4, 5, 6, 7, 8, 9, or 10 orders of magnitude. In some embodiments, the dynamic range of detection is greater than 10 orders of magnitude. In an embodiment, the detection limit is about 100 fM, with a dynamic range of 4 orders of magnitude of detection.

In an aspect of the invention, a computer system is provided for automatically detecting the presence and/or formation of a polymer having ABC dimers upon exposure of ABC monomers to a solution having a nucleic acid, such as a target (or complementary) nucleic acid (e.g., target DNA). In an embodiment, a user provides the ABC monomers to the solution and uses the computer system to determine whether the solution comprises the target nucleic acid. In an embodiment, the computer system makes this determination by detecting the presence of polymeric spheres. In an embodiment, the computer system interprets digital AFM images to determine whether polymeric spheres are present. In another embodiment, the computer system interprets microscope images (or micrographs) to determine whether the polymer is present. In an embodiment, the presence of the polymer indicates that a target nucleic acid was present in the solution that was tested.

One of skill in the art will appreciate that the modularity of the invention lends itself to any number of possible configurations which are envisioned by the invention. For example, a minimal monomer design could include a target recognition sequence and optionally a functional moiety to facilitate detection. In some embodiments, the monomers could be comprised solely of X-shaped nucleic acids, Y-shaped nucleic acids, T-shaped nucleic acids, or dumbbell shaped nucleic acids. Exemplary branched chain nucleic acids are presented in U.S. patent application Ser. No. 11/464,181 ("NUCLEIC ACID-BASED MATRIXES") to Luo et al., U.S. patent application Ser. No. 11/464,184 ("NUCLEIC ACID-BASED MATRIXES FOR PROTEIN PRODUCTION") to Luo et al., and PCT Patent Application PCT/US2009/52795, filed Aug. 5, 2009 and entitled "PHOTO-CROSSLINKING-BASED METHOD FOR CREATING DNA HYDROGELS," all of which are incorporated herein by reference in their entirety. Monomers comprised of combinations of such branched chain nucleic acid structures are also included within the scope of the invention.

EXAMPLES

Example 1

Functionalization of PEGA onto Y-DNA

PEGA (0.5 µM, 3,400 Da) was added into the solution containing 5' amine-modified Y-DNA (0.2 µM). The reaction was carried out overnight at room temperature. Non-reacted amine modified Y-DNA and PEGA were removed by HPLC equipped with a photo-diode array detector (Waters).

Example 2

Preparation of ABC Monomer and Dimer

ABC monomers were synthesized by incubating equimolar quantities of donor Y-DNA and corresponded bridge DNA with X-DNA at 30° C. for 1 hr. ABC dimers were assembled by mixing equimolar quantities of each ABC monomer with pathogen DNA in a solution containing 15 mM $MgCl_2$ and 10 mM Tris buffer (pH 8). The mixture was incubated at 30° C. for 30 min.

The nomenclature is as follows: $Y_{01}$, $Y_{02}$ and $Y_{03}$ are the three corresponding single oligonucleotide chains that form a Y-DNA. For formation of fluorescent-tagged Y-DNA, commercially synthesized fluorescent tagged oligonucleotide strands were used. Similarly, $X_{01}$, $X_{02}$, $X_{03}$ and $X_{04}$ are the four corresponding single oligonucleotide chains that form an X-DNA.

Example 3

Formation of ABC Polymer by Photo-Polymerization

ABC dimers were photo-polymerized at 265 nm UV light (8 m W/cm$^2$) in the presence of an initiator (Irgacure, Ciba Geigy, Ardsley, N.Y.) using a UV crosslinker (Spectronics corporation, XL-1000).

Example 4

Gel Electrophoresis

ABC monomers were run in a 3% agarose gel at 90 volts at 25° C. in Tris-acetate-EDTA (TAE) buffer (40 nM Tris, 20 nM acetic acid and 1 mM EDTA, pH 8.0, Bio-Rad, Hercules, Calif.).

Example 5

Scanning Transmission Electron Microscopy (STEM) Imaging

Samples were prepared by placing a 10 µl drop of the solution onto a copper grid coated with an ultra-thin carbon film and allowed to evaporate. Once the solution was completely evaporated, the sample was exposed to UV light for approximately 40 minutes to prevent contamination build-up during microscopy. STEM images were obtained using a 200 keV Tecnai F20 microscope with 1.6 Å resolution in annular dark-field STEM mode.

Example 6

Atomic Force Microscopy (AFM) Imaging

A 5 µl sample was placed onto the surface of freshly cleaved mica (Ted Pella, Redding, Calif.) functionalized with aminopropyltriethoxysilane (APTES, Aldrich, St. Louis, Mo.) and allowed to adsorb to the mica surface for approximately 20 minutes. The mica was then rinsed in Milli-Q water. Tapping-mode AFM images were taken in air using a Dimensions 3100 AFM (Digital Instruments, Santa Barbara, Calif.).

Example 7

Microscopy of Nano-Architectures

A 10 µl sample was placed onto the microscope glass and subsequently covered by a cover glass (22×22 mm$^2$). The DNA nano-architectures were observed with a microscope (Olympus IX70) equipped with 100× (high magnification) oil-immersion objectives. Images were acquired with Meta-Morph image acquisition software. All observations were performed at room temperature.

Example 8

Cell Culture

HeLa cells were cultured at 37° C. with 5% $CO_2$ in Dulbecco's Minimum Essential Medium (DMEM, Mediatech, Inc. Manassas, Va.) supplemented with 10% fetal bovine serum (FBS, Hyclone, Logan, Utah) and 2% penicillin/streptomycin (P/S, Mediatech, Inc, Manassas, Va.).

Example 9

Fluorescence Labeling and Imaging of Cell

Cells ($3\times10^4$) were cultured in each well on Lab-Tek chamber slide (8 wells, Permanox slide, Nunc) for one day. Cells were further cultured in the presence of 20 µl polymeric spheres (2.9 pM) over night at 37° C. at 4° C., or 10 min at 37° C. Cells were washed three times with PBS, and then fixed with 4% paraformaldehyde. Actin filaments and nucleus were stained with Alexa Fluor® 488 phalloidin (Invitrogen, Carlsbad, Calif.) and DAPI (4',6-diamidino-2-phenylindole) with antifade reagent (Invitrogen, Carlsbad, Calif.) according to the supplier's protocol. Cross-sectional images of the cell were obtained by confocal microscopy.

Example 10

Cell Cytotoxicity Evaluation

The cytotoxicity of the polymer spheres (with ABC monomer from 10 pM to 5 nM) was determined after 36 hours incubation with HeLa cells ($1\times10^4$ cell mL$^{-1}$) by measuring the release of lactate dehydrogenase (LDH) from a damaged membrane of cells using CytoTox-One™ Homogeneous membrane Integrity Assay (Promega, Madison, Wis.).

Example 11

Figure 6C:
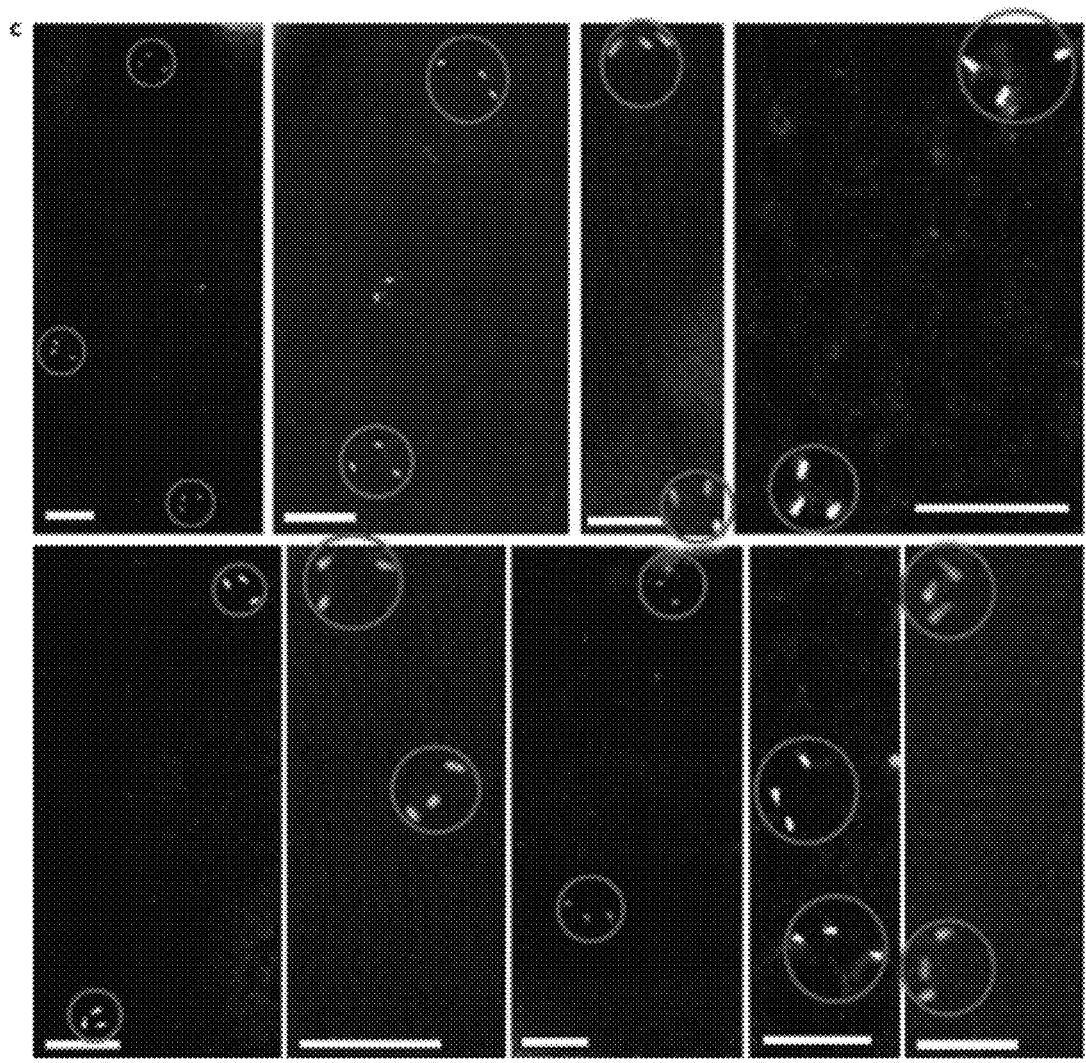
FIG. 6C illustrates annular dark-field STEM image of ABC monomers with three quantum dots. Scale bars, 100 nm. The measured distance based on STEM annular darkfield images was 44.8+7.3 nm, in accordance with an embodiment of the invention.
Figure 7A:
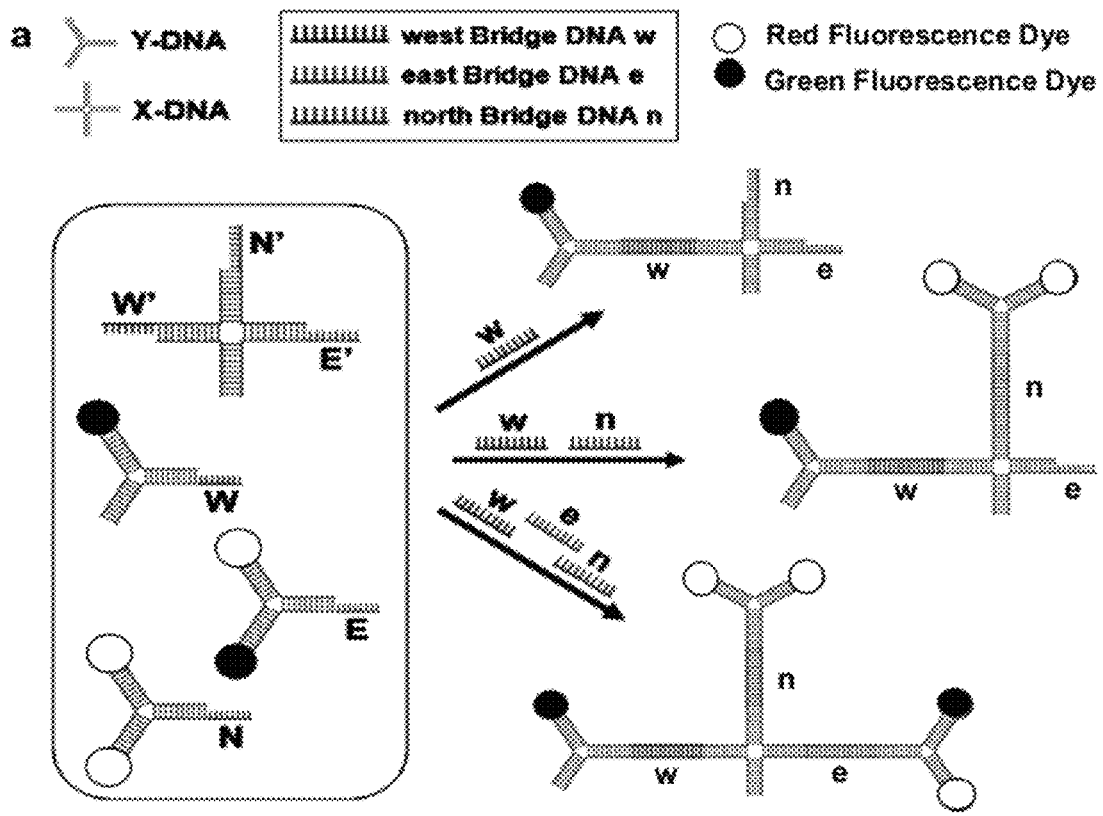
FIG. 7A presents a schematic drawing of synthesizing ABC monomers by controlling multi-moieties onto a single anisotropic X-DNA.
Figure 7B:
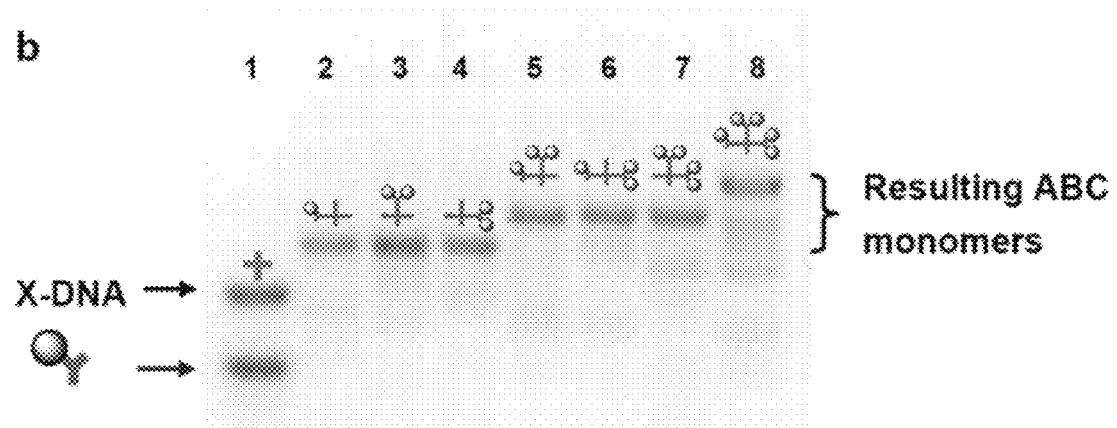
FIG. 7B illustrates gel electrophoresis migration pattern of ABC monomers after Ethidium Bromide (EtBr) staining, in accordance with an embodiment of the invention.

Creation of ABC Monomers Carrying Different Fluorescence Dyes with a Predetermined Ratio ABC monomers that within one monomer carried different fluorescence dyes with a predetermined ratio were created and characterized with gel electrophoresis (FIGS. 6a, 6b and 7b). The fluorescence colors of the ABC monomers corresponded to the combinations of donor Y-DNAs. Without adding bridge DNA, only unreacted Y-DNAs were shown (FIG. 6b, lane 1). Unreacted X-DNAs, which bore no fluorescence dyes, were dark and invisible but could be seen only after staining with a DNA specific dye, ethidium bromide (see FIG. 7b). After the bridge DNA was added to the reaction, a single green band appeared whose electrophoretic mobility was retarded (FIG. 6b, lane 2), suggesting that 1) green fluorescence dye was exclusively attached to the West branch of the X-DNA (X-W') and 2) the product was monodisperse. Similar results were obtained with fluorescence dye attached to the East and North branches of the X-DNA after adding n and e bridge DNA (FIG. 6b, lanes 3 and 4, respectively). To link two different configurations of fluorescence dyes simultaneously onto two different branches of a single X-DNA, two bridge DNAs were added simultaneously (FIG. 6b, lanes 5-7). By adding all three bridge DNAs, all three different donor Y-DNAs were anisotropically linked onto the X-DNA simultaneously (FIG. 6b, lane 8) in a controlled fashion. This approach is robust and efficient. The yield of ABC DNA monomers in this case, as estimated by densitometry, was about 90%.

Example 12

Characterization of the ABC Monomer at the Individual Molecule Level

To characterize the ABC monomer at the individual molecule level, donor Y-DNAs tethered with Au nanoparticles (AuNP) and two different types (colors) of QDs (see FIGS. 8 and 9) were generated to be linked onto X-DNAs.

Conjugation of Gold Nanoparticles with Oligonucleotide

AuNPs with a diameter of 5 nm were purchased from Ted. Pella. Inc. and functionalized. Oligonucleotides having an alkanedisulfide covalently bond to 3' ends were deprotected and incubated with 4.5 nM gold nanoparticles. The mixture was allowed to stand for 12 hours at room temperature. Then, sodium chloride was added to the mixture with a final concentration of 0.2M. The mixture was aged at room temperature for another 12 hours. The purpose of this procedure was also aimed to increase surface number density of oligonucleotides on gold nanoparticle surfaces. Then, the mixture was centrifuged and exchanged into Milli-Q water. According to O.D. of released oligonucleotides by DTT, a 150 number density of ssDNA/particle was achieved. The as-prepared oligonucleotide modified gold nanoparticles were ready to be attached with donor Y-DNA Conjugation of Quantum Dots (QDs) with Y-DNA The QD and Y-DNA conjugation was performed by direct association of biotinylated Y-DNA to streptavidin-coated QDs (Invitrogen Corporation, Carlsbad, Calif.). Because of the highly specific interaction between streptavidin and biotin, the yield of conjugation is high. 20 pmole of Y-DNA was reacted with 10 µl of 1 µM QD solution in 10 mM PBS overnight at room temperature. Non-reacted biotinylated Y-DNA was removed by a streptavidin affinity column (Promega, Madison, Wis.). Y03 5'/phos/- can be ACTG, ACTC, AGTG, AGTC (e.g., Table 2 for Y-DNA (QD)). Furthermore, $X_{04}$ 5'-/phos/- can be CAGT or GAGT (e.g., Table 2, X DNA).

Both nanoparticles were individually visible via scanning transmission electron microscopy (STEM). In addition, QDs were visible at both the bulk and solution scales through their intrinsic fluorescence (FIG. 9b and c). With reference to FIG. 6c, the multi-moieties within one ABC monomer were obviously tethered together at the expected distance from one another (with reference to FIG. 10, two 15 nm rod-shaped QDs and one 5 nm round-shaped AuNP are tethered together and are within the expected distance). These images show that different multi-moieties were individually and anisotropically placed at the accurate position within one ABC monomer.

Example 13

Synthesis of Multifunctional Nano-Architectures for Pathogen Sensing

To synthesize multifunctional nano-architectures from an ABC monomer, each ABC monomer was designed to have two QDs with three different color configurations (2G, 1G1R, or 2R), one photo-responsive PEGA (polyethylene glycol monoacrylate) moiety, and one single-stranded oligonucleotide probe that is complementary to a specific pathogen DNA such as SARS coronavirus, Ebola virus, or *Bacillus anthracis* (this unique DNA is termed "capture probe", see 1A and 1B in FIG. 2a, and FIG. 12 for sequences).

Consequently, an ABC dimer formed only in the presence of a targeted pathogen DNA because the pathogen DNA now served as a bridge or linking DNA to link the two ABC monomers (such as monomers 1A and 1B of FIG. 2a) together to form a dimer (such as dimer 2 of FIG. 2a). Upon a short UV illumination (10 min), polymerization occurred with the dimers (e.g., FIG. 2a, species 3) but not with the undimerized monomers (e.g., FIG. 2a, species 5). A "target-driven" polymerization method has thus been demonstrated, where polymers (diblock co-polymer here) can only be synthesized in the presence of a specific target DNA. The polymerization was dependent on a pathogen DNA.

Atomic force microscopy was used to image the morphology of the pathogen-target-driven polymer. The image shows that the polymerized ABC monomers were nearly spherical in shape (FIG. 2b). Dynamic light scattering measurement revealed that the average diameter was about 410±70 nm (FIG. 2c). Because each monomer contained two specific QDs with a pre-determined ratio (1G1R), the formation of the target-driven polymers was further evaluated by both bright-field and epi-fluorescence optical microscopy (FIGS. 2d and e). The overlay of bright-field and fluorescence images confirmed again that the polymeric spheres were generated from ABC monomers due to the unique 1G1R fluorescence ratio (FIG. 2e, where the left box is 'green' and the right box is 'red').

Besides being able to link several hundred QDs together thus effectively amplifying signals from a single target-binding event, each target-driven polymer also contains a unique fluorescence code with a specific ratio of green and red, which makes it possible to detect multiple targets simultaneously. Here, three different pathogen DNAs (SARS, Ebola, and Anthrax) were used as target DNAs (for sequences see FIG. 12). An "unknown" DNA was first added and after the target-driven photo-polymerization the resultant spheres possessed a color ratio of 1G1R (FIG. 13a). By referring to the pre-assigned fluorescence codes (see FIG. 21), this result indicated that the "unknown" DNA was SARS DNA. Similarly, Anthrax and Ebola DNA were detected with 1G3R and 4G0R, respectively (see FIGS. 13b and 13c). The detection was highly specific: in the presence of an unrelated DNA, no polymerized sphere was observed (FIG. 13d) because polymerization could not occur with only mono-PEGA-ABC monomers. The concentration of polymeric spheres (i.e., the number of spheres per unit area from microscopy images) was linearly proportional to the log of concentrations of target DNA. Thus, the presence of the pathogen DNA can be detected by counting the polymeric spheres under the microscope. The estimated detection limit was about 100 fM at the current conditions (FIG. 13e). Moreover, this method allows for a wide dynamic range (4 orders of magnitude) of detection.

Example 14

ABC Monomers for Drug Delivery

Polymerized spheres were delivered to cells with both model drugs and tracers (oligodeoxynucleotides and QDs, respectively). Microscopy images revealed that similar-sized spheres were internalized by HeLa cells (FIGS. 14a-c). Uptake of spheres was probably due to endocytosis because no fluorescence was observed inside cells when endocytosis was inhibited (FIGS. 15a and b). These results suggest that cells can uptake these multi-drug carriers without any special treatment such as a transfection reagent. Also, the ABC polymers exhibit little cytotoxicity. After 36 hour treatment with ABC monomers, HeLa cells showed less than 10% cytotoxicity (FIG. 14d). With conditions reported here, the efficiency of delivery reached 25%. The ABC polymers provide a general platform to carry different moieties within one entity for both delivering and tracing.

Example 15

Synthesis of Y-DNA Donor and X-DNA Acceptor

Y-DNA donor and X-DNA acceptor were fabricated according to methods described in the Luo publications (see above). In a typical experiment, the Y-DNA donor was synthesized by mixing the same molar amount of corresponding oligonucleotide strands. The nomenclature is as follows: $Y_{01}$, $Y_{02}$ and $Y_{03}$ are the three corresponding single oligonucleotide chains that form a Y-DNA. To form fluorescent tagged Y-DNA, commercially synthesized fluorescent tagged oligonucleotide strands were used. Similarly, $X_{01}$, $X_{02}$, $X_{03}$ and $X_{04}$ are the four corresponding single oligonucleotide chains that form an X-DNA. All strands including biotinylated and amine modified strands were purchased from IDT (Integrated DNA Technologies, Coralville, Iowa).

Example 16

Conjugation of PEGA onto Y-DNA

Figure 3:
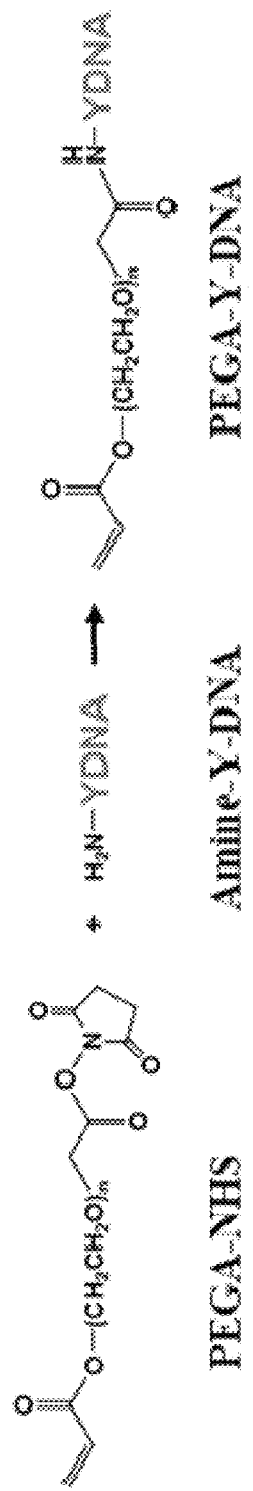
FIG. 3 illustrates the synthesis of PEGA-modified Y-DNA, in accordance with an embodiment of the invention.

Acrylate-(polyethylene glycol)-succinimidyl carboxy methyl ester is a set of compounds having polyethylene glycol (PEG) spacers with monoacrylate (PEGA) and amine-reactive N-hydroxysuccinimide (NHS)-ester groups at opposite ends (FIG. 3). The NHS-ester is spontaneously reactive with primary amines (—NH2) of Y-DNA, providing an efficient route for conjugation. To tether the PEGA to Y-DNA, 0.5 µM PEGA-NHS (3,400 Da) was added into the solution containing 0.2 µM 5' amine-modified Y-DNA (NH2-Y-DNA). The reaction was carried out overnight at room temperature. PEGA-Y-DNA was separated from non-reacted NH2-Y-DNA and PEGA by an HPLC XBridge C18 column equipped with a photo-diode array detector (Waters). The HPLC chromatogram was obtained (FIG. 4A) from a gradient elution from 0-50% acetonitrile in 0.1 M triethylammonium acetate (TEAA, pH 7.0) as the mobile phase within 40 min at a flow rate of 0.5 mL/min with UV detection (260 nm). Multiple peaks are observed in FIG. 4A because the arms of Y-DNA are double helixes, and they can breathe (partially zip and unzip the structure) at room temperature. However, the resulting products show a single major band in gel electrophoresis in FIG. 4B. Lane 1 indicates $NH_2$—Y-DNA (from HPLC fraction B) and lane 2 indicates PEGA-Y-DNA (from HPLC fractions C1-C2). Compared to NH2-Y-DNA, the gel electrophoretic mobility of PEGA-Y-DNA was retarded, as expected, because of the increase of molecular weight.

FTIR spectrum of PEGA-Y-DNA (FIG. 5) revealed several transmission bands from an amide bond, PEG, and DNA. Two characteristic bands of C=O and N—H groups were observed at 1672 and 1620 cm-1 for amide bond. The transmission bands at higher wave numbers were assigned to the amide I band and the bands at lower wave numbers to the amide II band, which is typical of primary amides. Another transmission band at 2881 cm-1 was assigned to the CH2 group of PEG. The transmission bands at 1080 and 1252 cm-1 were assigned to the PO2 group of DNA. The appearance of a new amide bond confirmed the formation of PEGA-Y-DNA.

Example 17

Synthesize ABC Monomer with Fluorescence Dyes and Investigate the Selectivity

Seven different ABC monomers were synthesized and characterized via gel electrophoresis (3% agarose gel at 90 volts at 25° C. in Tris-acetate-EDTA (TAE) buffer (40 nM Tris, 20 nM acetic acid and 1 mM EDTA, pH 8.0, Bio-Rad, Hercules, Calif.)). First, 1.5 µM X-DNA and three different types of 1.5 µM Y-DNA (one green (1G), two reds (2R), and one green and one red (1G1R)) were incubated (FIG. 7A). Second, specific Y-DNA was connected to X-DNA by adding 1.5 µM specific bridge DNA which was complementary to the sticky end of both X- and Y-DNA. Without bridge DNA, X- and Y-DNA were not linked (Lane 1 in FIG. 7B). For example, only 1G Y-DNA were connected to X-DNA by adding w bridge DNA. Both 1G and 2R Y-DNA were liked to one X-DNA by adding w and n bridge DNA. The ABC monomer, which consisted of three Y-DNA by adding all three bridge DNA, was selected for further experiments (Lane 8 in FIG. 7B).

Example 18

Conjugation of Quantum Dots (QDs) with Y-DNA

QDs were from Invitrogen (Carlsbad, Calif.). The QDs were commercially coated with streptavidin. The emission wavelengths of the green QD (Qdot® 525 streptavidin conjugate) and the red QD (Qdot® 655streptavidin conjugate) were 525 nm and 655 nm, respectively. In the structure of the QD, the CdSe core is encapsulated in a shell of ZnS and the polymer shell (FIG. 8) and the outside was covalently conjugated with streptavidin. The QD and Y-DNA conjugation was performed by direct association of biotinylated Y-DNA to streptavidin-coated QDs. Because of the highly specific interaction between streptavidin and biotin, the yield of conjugation is high. 20 pmole of Y-DNA was reacted with 10 µl of 1 µM QD solution in 10 mM PBS overnight at room temperature. Non-reacted biotinylated Y-DNA was removed by a streptavidin affinity column (Promega, Madison, Wis.).

Example 19

Synthesize ABC Monomers with Nanoparticles

To synthesize ABC monomers with three quantum dots, the south branch of the X-DNA was first anchored onto a solid bead 1 (FIG. 9a). Both west and east end-sequences of X-DNA were then connected with Y-DNA donor tethering green quantum dots. The end-sequence at the north of an X-DNA was connected with red QD Y-DNA. The ABC monomers attached to the beads 3 were released by a restriction enzyme Dde I digestion and the isolated ABC monomers 4 were collected. This solid phase synthesis was modified according to previously reported methods. See Um, S. H., Lee, J. B, Kwon, S., Li, Y; Luo, D. Nat Protocols 1. 995-1000 (2006).

Example 20

Scanning Transmission Electron Microscopy (STEM) Imaging

Samples were prepared by placing a 10 µl drop of the ABC monomer solution onto a copper grid coated with an ultra-thin carbon film and allowed to evaporate. Once the solution was completely evaporated, the sample was exposed to UV light for approximately 40 minutes to prevent contamination build-up during microscopy. STEM images were obtained on a 200 keV Tecnai F20 microscope with 1.6 Å resolution in annular dark-field STEM mode.

Example 21

Loading ODN to Polymeric Spheres

Figure 16:
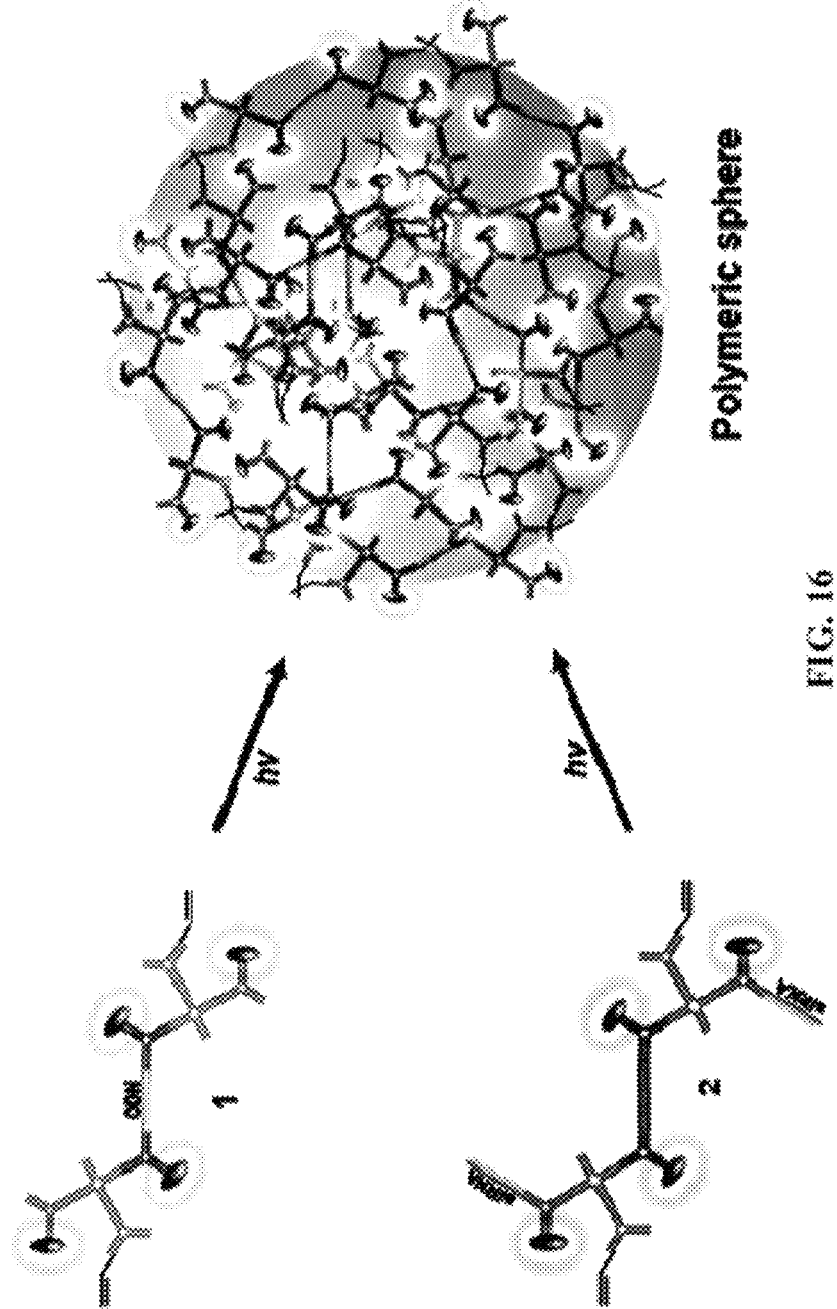
FIG. 16 illustrates a schematic drawing of nucleic-acid-based drug loading into polymeric spheres with oligodeoxynucleotide (ODN) (1) or small interfering ribonucleic acid (siRNA) (2). Both ODN and siRNA can be loaded in the sphere by hybridization, in accordance with an embodiment of the invention.

To load drug (oligonucleotide, ODN) in spherical polymers, the ODNs were hybridized to the sticky end of ABC monomers first. Then, the spherical polymers were able to carry the hybridized ODN in a cluster format by photo-polymerization (FIG. 16).

Example 22

Investigation of Endocytosis Mechanism of the Polymeric Spheres Uptake

To investigate the cellular endocytosis mechanism of the polymeric spheres, HeLa cells ($5 \times 10^4$) were cultured in each well on Lab-Tek chamber slide (8 wells, Permanox slide, Nunc) overnight. Cells were pre-incubated with endocytosis inhibitors for 30 min with 10 µg/mL of chlorpromazine hydrochloride (Sigma) and 5 µg/mL of filipin complex (Sigma), and for 1 hr with 0.5 µg/mL of Cytochalasin B and 0.1% of DMSO as a positive control. Cells were then cultured with 20 µL of polymeric spheres (2.9 pM) and each inhibitor for 3 hrs. The number of cells uptaking the spheres was counted from fluorescent microscope images after staining with the same method described in materials and method in the main manuscript.

Figure 17:
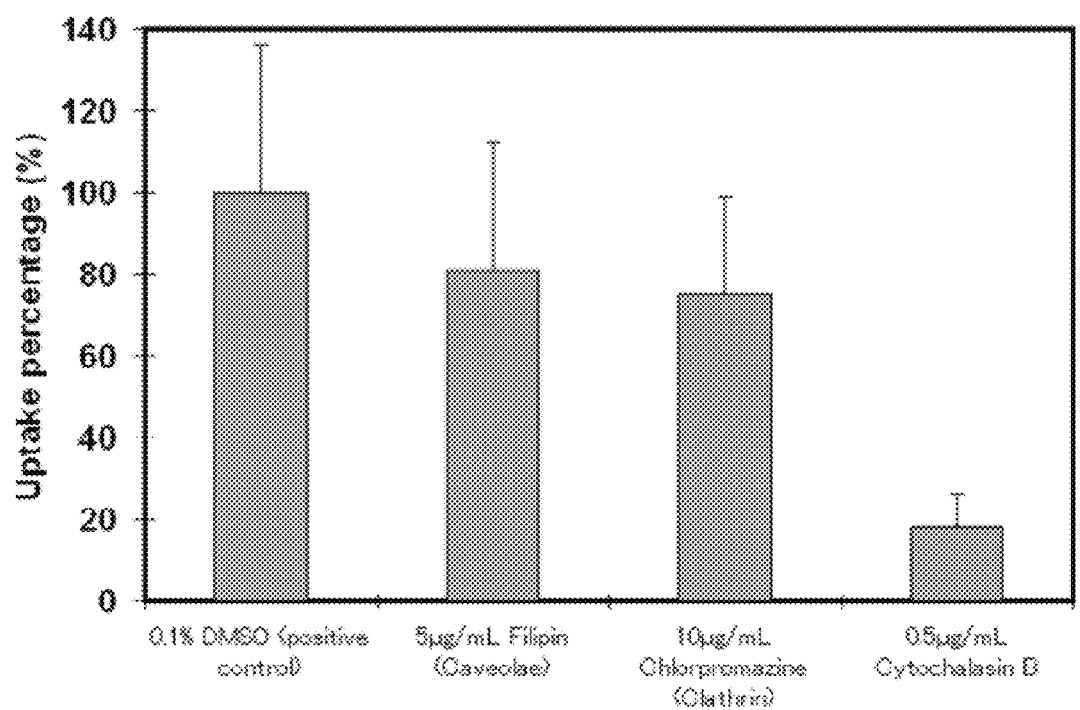
FIG. 17 illustrates cellular uptake of polymeric spheres in the presence of various endocytosis-specific inhibitors, in accordance with an embodiment of the invention.

The cellular endocytosis mechanism of polymeric spheres was studied by inhibition experiments. Cells were incubated with chlorpromazine to inhibit the clathrin-mediated endocytosis pathway and with filipin complex to inhibit caveolae-mediated endocytosis. Cytochalasin B was used to disrupt actin-mediated endocytosis. As seen in FIG. 17, chlorpromazine and filipin did not reduce the uptake of spheres, while cytochalasin B significantly reduced cellular uptake of the spheres. Actin-dependent endocytosis such as phagocytosis and macropinocytosis may be the main mechanism for the cellular uptake.

Example 23

Dynamic Light Scattering Measurements

Dynamic light scattering (DLS) data of the ABC monomers and polymeric spheres were obtained. DLS measurements were performed using the Zetasizer Nano instrument (Malvern) with 500 µl of the samples at 25° C. An increase of size of the polymeric spheres was observed after photo-polymerization (FIG. 18a). FIG. 18b shows changes of polymeric sphere sizes with different concentrations of ABC monomers.

While preferable embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method for detecting the presence of a target nucleic acid, comprising:
   providing a first monomer and a second monomer to a solution comprising the target nucleic acid, each of the first and second monomers formed from an X-shaped nucleic acid and one or more Y-shaped nucleic acids, wherein the first monomer links to the second monomer with the aid of the target nucleic acid to form a dimer; and
   polymerizing the dimer to form a polymer;
   wherein polymerizing the dimer comprises photo-polymerizing the dimer.

2. The method of claim 1, wherein the X-shaped and Y-shaped nucleic acids comprise deoxyribonucleic acid (DNA), ribonucleic acid (RNA), peptide nucleic acid (PNA), or a combination thereof.

3. The method of claim 1, wherein the first and/or second monomers comprises a Y-shaped nucleic acid having a crosslinkable moiety.

4. The method of claim 3, wherein the crosslinkable moiety includes a photoreactive group.

5. The method of claim 1, wherein the first and/or second monomer comprises a X-shaped or Y-shaped nucleic acid having a functional moiety.

6. The method of claim 5, wherein the functional moiety comprises a DNA capture probe, a fluorescent dye, a quantum dot, a gold nanoparticle, a peptide, a polypeptide, a protein, a lipid, a carbohydrate, an aptamer, an antibody, an antigen, a cell growth factor, a DNA binding agent, a detectable label, a selectable marker, biotin, a biologically active agent, a pharmaceutical agent, a drug, a small molecule, a therapeutic agent, a receptor molecule, a ligand, or a nucleic acid molecule.

7. The method of claim 1, further comprising detecting the presence of the polymer.

8. The method of claim 7, wherein detecting the presence of the polymer comprises detecting the presence of one or more functional moieties of one or both of the first and second monomers.

9. The method of claim 7, wherein detecting the presence of the polymer comprises detecting fluorescent light.

10. The method of claim 1, wherein each of the first and second monomers is formed by hybridizing an acceptor sequence of an X-shaped nucleic acid with a donor sequence of a Y-shaped nucleic acid.

11. The method of claim 10, wherein the X-shaped nucleic acid is hybridized to the Y-shaped nucleic acid with the aid of a bridge DNA having a sequence complementary to the donor sequence of the Y-shaped nucleic acid and the acceptor sequence of the X-shaped nucleic acid.

12. The method of claim 1, wherein the first monomer links to the second monomer via hybridization of the target nucleic acid with the first and second monomers.

13. The method of claim 1, wherein the target nucleic acid has a sequence that is partially complementary to a linking sequence of the first monomer and partially complementary to a linking sequence of the second monomer.

14. The method of claim 1, wherein the target nucleic acid comprises at least a portion of a pathogen nucleic acid.

15. The method of claim 1, wherein each of the first and second monomers is formed from an X-shaped nucleic acid and a plurality of Y-shaped nucleic acids.

16. The method of claim 15, wherein the plurality of Y-shaped nucleic acids comprises 2, 3 or 4 Y-shaped nucleic acids.

17. The method of claim 1, wherein polymerizing the dimer comprises exposing a plurality of the dimers to electromagnetic radiation.

18. The method of claim 17, wherein the electromagnetic radiation comprises ultraviolet (UV) light, visible light, near infrared, infrared, microwaves, gamma rays, X-rays, or radio waves.

* * * * *